United States Patent
Trainor et al.

(10) Patent No.: US 12,247,188 B2
(45) Date of Patent: Mar. 11, 2025

(54) CELL CULTURE CHAMBER WITH IMPROVED CELL-CONTACTING SURFACES

(71) Applicants: OCTANE BIOTECH INC., Kingston (CA); LONZA WALKERSVILLE, INC., Walkersville, MD (US)

(72) Inventors: Nuala Trainor, Kingston (CA); Eytan Abraham, Walkersville, MD (US); Timothy Smith, Kingston (CA); Matthew Hewitt, Walkersville, MD (US); Yaling Shi, Walkersville, MD (US); Kelly Purpura, Kingston (CA); Chase McRobie, Kingston (CA)

(73) Assignees: OCTANE BIOTECH INC., Kingston (CA); LONZA WALKERSVILLE, INC., Walkersville, MD (US)

( * ) Notice: Subject to any disclaimer, the term of this patent is extended or adjusted under 35 U.S.C. 154(b) by 251 days.

(21) Appl. No.: 17/077,447

(22) Filed: Oct. 22, 2020

(65) Prior Publication Data
US 2021/0123008 A1    Apr. 29, 2021

Related U.S. Application Data

(60) Provisional application No. 62/925,392, filed on Oct. 24, 2019.

(51) Int. Cl.
*C12M 3/00* (2006.01)
*C12M 1/00* (2006.01)
(Continued)

(52) U.S. Cl.
CPC ............ *C12M 23/04* (2013.01); *C12M 23/20* (2013.01); *C12M 23/24* (2013.01); *C12M 23/42* (2013.01);
(Continued)

(58) Field of Classification Search
CPC .............................. C12M 23/04; C12M 23/24
See application file for complete search history.

(56) References Cited

U.S. PATENT DOCUMENTS

| 4,642,120 A | 2/1987 | Nevo et al. |
| 4,939,151 A | 7/1990 | Bacehowski et al. |

(Continued)

FOREIGN PATENT DOCUMENTS

| AU | 2002/324169 A1 | 3/2003 |
| DE | 4021123 A1 | 4/1991 |

(Continued)

OTHER PUBLICATIONS

Konstantin B. Konstantinov "Monitoring and Control of the Physiological State of Cell Cultures" Biotechnology and Bioengineering, vol. 52, pp. 271-289 (1996) (Year: 1996).

(Continued)

*Primary Examiner* — Nathan A Bowers
(74) *Attorney, Agent, or Firm* — MEDLER FERRO WOODHOUSE & MILLS

(57) ABSTRACT

The present disclosure provides cell culture chambers for use in automated cell engineering systems, and in particular, cell culture chambers that include improved cell-contacting surfaces. Improved cell-contacting surfaces can include a surface coating that promotes cell growth, adherence, differentiation, maintenance of phenotype, and/or improves transduction; a cell-contacting surface comprising a non-porous, gas-permeable material; as well as other modifications to the cell-contacting surfaces. Cassettes comprising the cell culture chambers are also provided.

20 Claims, 15 Drawing Sheets

(51) Int. Cl.

| | | |
|---|---|---|
| *C12M 1/02* | (2006.01) | |
| *C12M 1/04* | (2006.01) | |
| *C12M 1/12* | (2006.01) | |
| *C12M 1/34* | (2006.01) | |
| *C12M 1/36* | (2006.01) | |
| *C12N 5/00* | (2006.01) | |
| *G01N 35/10* | (2006.01) | |

(52) U.S. Cl.
CPC .......... *C12M 27/00* (2013.01); *C12M 29/24* (2013.01); *C12M 41/12* (2013.01); *C12M 41/32* (2013.01); *C12M 41/34* (2013.01); *C12M 41/48* (2013.01); *C12N 5/0068* (2013.01); *G01N 35/1009* (2013.01); *C12N 2533/52* (2013.01)

(56) References Cited

U.S. PATENT DOCUMENTS

| | | |
|---|---|---|
| 5,041,138 A | 8/1991 | Vacanti et al. |
| 5,081,036 A | 1/1992 | Familletti |
| 5,240,854 A | 8/1993 | Berry et al. |
| 5,246,699 A | 9/1993 | Debre et al. |
| 5,424,209 A | 6/1995 | Kearney |
| 5,478,479 A | 12/1995 | Herrig |
| 5,549,134 A | 8/1996 | Browne et al. |
| 5,688,687 A | 11/1997 | Palsson et al. |
| 5,728,581 A | 3/1998 | Schwartz et al. |
| 5,786,207 A | 7/1998 | Katz et al. |
| 5,792,603 A | 8/1998 | Dunkelman et al. |
| 5,827,729 A | 10/1998 | Naughton et al. |
| 5,842,477 A | 12/1998 | Naughton et al. |
| 5,846,828 A | 12/1998 | Peterson et al. |
| 5,882,929 A | 3/1999 | Fofonoff et al. |
| 5,891,455 A | 4/1999 | Sittinger et al. |
| 5,902,741 A | 5/1999 | Purchio et al. |
| 5,906,934 A | 5/1999 | Grande et al. |
| 5,922,604 A | 7/1999 | Stapleton et al. |
| 5,928,936 A | 7/1999 | Ingram |
| 5,935,847 A * | 8/1999 | Smith ................ C12M 23/20 435/297.5 |
| 5,985,653 A | 11/1999 | Armstrong et al. |
| 5,989,913 A | 11/1999 | Anderson et al. |
| 5,994,129 A | 11/1999 | Armstrong et al. |
| 6,048,721 A | 4/2000 | Armstrong et al. |
| 6,048,722 A | 4/2000 | Farb et al. |
| 6,060,306 A | 5/2000 | Flatt et al. |
| 6,096,532 A | 8/2000 | Armstrong et al. |
| 6,121,042 A | 9/2000 | Peterson et al. |
| 6,123,655 A | 9/2000 | Fell |
| 6,197,575 B1 | 3/2001 | Griffith et al. |
| 6,214,574 B1 | 4/2001 | Kopf |
| 6,228,635 B1 | 5/2001 | Armstrong et al. |
| 6,238,908 B1 | 5/2001 | Armstrong et al. |
| 6,297,046 B1 | 10/2001 | Smith et al. |
| 6,323,146 B1 | 11/2001 | Pugh et al. |
| 6,402,941 B1 | 6/2002 | Lucido et al. |
| 7,348,175 B2 | 5/2008 | Vilendrer et al. |
| 7,560,274 B1 * | 7/2009 | Fuller ................ C12M 25/02 435/297.5 |
| 7,906,323 B2 | 3/2011 | Cannon et al. |
| 9,629,877 B2 | 4/2017 | Cooper et al. |
| 10,131,876 B2 | 11/2018 | Kaiser et al. |
| 10,253,316 B2 | 4/2019 | Masquelier et al. |
| 10,273,300 B2 | 4/2019 | Bedoya et al. |
| 11,208,626 B2 | 12/2021 | Mason et al. |
| 2001/0021529 A1 | 9/2001 | Takagi |
| 2001/0043918 A1 | 11/2001 | Masini et al. |
| 2002/0009797 A1 | 1/2002 | Wolf et al. |
| 2002/0009803 A1 | 1/2002 | Gabor Vajta |
| 2002/0025547 A1 | 2/2002 | Rao |
| 2002/0037580 A1 | 3/2002 | Schoeb |
| 2002/0146816 A1 | 10/2002 | Vellinger et al. |
| 2002/0155487 A1 | 10/2002 | Greenberger et al. |
| 2002/0179525 A1 | 12/2002 | Shaffer et al. |
| 2003/0008388 A1 * | 1/2003 | Barbera-Guillem ... C12M 23/58 435/297.5 |
| 2003/0032071 A1 | 2/2003 | Wang et al. |
| 2003/0040104 A1 | 2/2003 | Barbera-Guillem |
| 2003/0054335 A1 | 3/2003 | Taya et al. |
| 2003/0159946 A1 | 8/2003 | Eden et al. |
| 2003/0215935 A1 | 11/2003 | Coon |
| 2004/0048364 A1 | 3/2004 | Trosch |
| 2005/0064465 A1 | 3/2005 | Dettloff et al. |
| 2005/0106717 A1 * | 5/2005 | Wilson ................ C12M 25/06 435/297.5 |
| 2005/0130297 A1 | 6/2005 | Sarem et al. |
| 2005/0186671 A1 | 8/2005 | Cannon et al. |
| 2008/0227176 A1 * | 9/2008 | Wilson ................ C12M 23/08 435/243 |
| 2009/0148941 A1 * | 6/2009 | Florez ................ C12M 23/24 435/325 |
| 2010/0055774 A1 * | 3/2010 | Wilson ................ C12M 23/24 435/289.1 |
| 2011/0198286 A1 * | 8/2011 | Niazi ................ C12M 29/06 210/638 |
| 2013/0059339 A1 * | 3/2013 | Karerangabo ......... C12M 25/06 435/70.1 |
| 2013/0084030 A1 * | 4/2013 | Staheli ................ C12M 23/14 383/105 |
| 2014/0120608 A1 * | 5/2014 | Carter ................ C12M 3/00 435/289.1 |
| 2015/0344844 A1 | 12/2015 | Better et al. |
| 2016/0122782 A1 | 5/2016 | Crisman et al. |
| 2016/0319234 A1 * | 11/2016 | Song ................ C12M 27/16 |
| 2017/0037369 A1 | 2/2017 | Ramsborg et al. |
| 2017/0051252 A1 | 2/2017 | Morgan et al. |
| 2019/0211294 A1 | 7/2019 | Karnieli |
| 2019/0249130 A1 | 8/2019 | Griffin et al. |
| 2019/0358633 A1 * | 11/2019 | Collins ................ C12M 47/10 |
| 2020/0208095 A1 * | 7/2020 | Oram ................ C12M 21/08 |
| 2021/0147785 A1 * | 5/2021 | Buzalewicz .......... C12M 41/12 |

FOREIGN PATENT DOCUMENTS

| | | |
|---|---|---|
| EP | 0248675 A1 | 12/1987 |
| GB | 1356794 A | 6/1974 |
| JP | 2-119772 A | 5/1990 |
| JP | 2-174848 A | 7/1990 |
| JP | 3-500847 A | 2/1991 |
| JP | 5-503418 A | 6/1993 |
| JP | 6-54678 A | 3/1994 |
| JP | 6-261736 A | 9/1994 |
| JP | 7-501206 A | 2/1995 |
| JP | H08-56646 A | 3/1996 |
| JP | H11-507229 A | 6/1999 |
| JP | 2001-275659 A | 10/2001 |
| JP | 2001-517428 A | 10/2001 |
| JP | 2002-500004 A | 1/2002 |
| JP | 2004147555 A | 5/2004 |
| KR | 200243145 Y1 | 9/2001 |
| WO | 91/05849 A1 | 5/1991 |
| WO | 93/03142 A1 | 2/1993 |
| WO | 1997/12960 A2 | 4/1997 |
| WO | 99/33951 A1 | 7/1999 |
| WO | 99/47922 A2 | 9/1999 |
| WO | 2000/046349 A1 | 8/2000 |
| WO | 01/02030 A2 | 1/2001 |
| WO | 2001/000783 A2 | 1/2001 |
| WO | 2002/028996 A1 | 4/2002 |
| WO | 02/088295 A1 | 11/2002 |
| WO | 03/022985 A2 | 3/2003 |
| WO | 03/087292 A2 | 10/2003 |
| WO | 2003/085101 A1 | 10/2003 |
| WO | 2013/151755 A1 | 10/2013 |
| WO | 2015/162211 A1 | 10/2015 |
| WO | 2016/069993 A1 | 5/2016 |
| WO | 2016/118780 A1 | 7/2016 |
| WO | 2016/168275 A1 | 10/2016 |
| WO | 2017/068425 A1 | 4/2017 |

(56) References Cited

FOREIGN PATENT DOCUMENTS

| WO | 2018/015561 A1 | 1/2018 |
| WO | 2018/136566 A1 | 7/2018 |
| WO | 2019/046766 A2 | 3/2019 |

OTHER PUBLICATIONS

Farndale "Pulsed Electromagnetic Fields Promote Collagen Production in Bone Marrow Fibroblasts via Athermal Mechanisms" Calcif Tissue Int (1985) 37:178-182.

Shi et al., Performance of Mammalian Cell Culture Bioreactor with a New Impeller Design, Biotechnology and Bioengineering, Jun. 20, 1992, pp. 260-270, vol. 40, John Wiley & Sons, Inc.

Declaration from Mark Selker, Submitted in *Lonza Walkersville, Inc.* v. *Adva Biotechnology LTD.*, United States District Court for the District of Maryland, Case No. 8:20-cv-03099-PX, Jan. 5, 2022.

Declaration from James C. Leung, Submitted in *Lonza Walkersville, Inc.* v. *Adva Biotechnology LTD.*, United States District Court for the District of Maryland, Case No. 8:20-cv-03099-PX, Jan. 7, 2022.

Aitken-Christie et al., Automation in Plant tissue culture—general introduction and overview, in Automation and Environmental Control in Plant Tissue Culture 757 (J. Aitken-Christie, T. Kozai & M. Lila Smith eds., 1995).

Apel et al., Integrated Clinical Scale Manufacturing System for Cellular Products Derived by Magnetic Cell Separation, Centrifugation and Cell Culture, Chemie Ingenieur Technik (2013).

Armstrong et al., Clinical Systems for the Production of Cells and Tissues for Human Therapy, in Novel Therapeutics From Modern Biotechnology 221 (D.L. Oxender et al. eds., 1999).

Blaeschke et al., Induction of A Central Memory and Stem Cell Memory Phenotype in Functionally Active CD4+ and CD8+ CAR T Cells Produced in an Automated Good Manufacturing Practice System for the Treatment of CD19+ Acute Lymphoblastic Leukemia, Cancer Immunology, Immunotherapy vol. 67, pp. 1053-1066 (2018), published Mar. 31, 2018.

Bohnenkamp et al., Bioprocess development for the cultivation of human T-lymphocytes in a clinical scale, Cytotechnology (2002).

Bousso, T-cell activation by dendritic cells in the lymph node: lessons from the movies, 8 Nature Reviews Immunology 675 (2008) ("Bousso 2008").

Basic and Clinical Immunology: Antigen Presentation, T Cell Activation and Deactivation, CLEVELANDCLINICCME, found at https://www.youtube.com/watch?v=EfYpkA4AmFo (2017), last visited Dec. 6, 2020 ("Cleveland Clinic video").

Kaiser et al., Towards a Commercial Process for the Manufacture of Genetically Modified T Cells for Therapy, 22 Cancer Gene Therapy 72-78 (2015).

Kempner et al., A Review of Cell Culture Automation, 7 Journal of the Association for Laboratory Automation 56 (2002) ("Kempner 2002").

Koller et al., Clinical-scale human umbilical cord blood cell expansion in a novel automated perfusion culture system, Bone Marrow Transplantation (1998) ("Koller 1998").

Koller et al., Large-Scale Expansion of Human Stem and Progenitor Cells from Bone Marrow Mononuclear Cells in Continuous Perfusion Cultures, Blood (1993) ("Koller 1993A").

Koller et al., Tissue Engineering: Reconstitution of Human Hematopoiesis Ex Vivo, Biotechnology and Bioengineering (1993) ("Koller 1993B").

Kostov et al., Low-Cost Microbioreactor for High-Throughput Bioprocessing, 72 Biotechnology and Bioengineering, Feb. 5, 2001 ("Kostov 2001").

Krug et al., A GMP-compliant protocol to expand and transfect cancer patient T cells with mRNA encoding a tumor-specific chimeric antigen receptor, Cancer Immunol Immunotherapy (2014) ("Krug 2014").

Levine et al., Global Manufacturing of CAR T Cell Therapy, 4 Molecular Therapy: Methods & Clinical Development 92 (2017).

Lock et al., Automated Manufacturing of Potent CD20-Directed Chimeric Antigen Receptor T Cells for Clinical Use, 28 Human Gene Therapy 10 (2017), ("Lock 2017").

Lu et al., A Rapid Cell Expansion Process for Production of Engineered Autologous CART Cell Therapies, 27 Human Gene Therapy 6 (2016).

Mock et al., Automated manufacturing of chimeric antigen receptor T cells for adoptive immunotherapy using CliniMACS Prodigy, Cytotherapy (2016).

Morse, Technology evaluation: Stem-cell therapy, Aastrom Biosciences Inc., Current Opinion in Molecule Therapeutics (1999) ("Morse 1999").

Oh et al., Frequent Harvesting from Perfused Bone Marrow Cultures Results in Increased Overall Cell and Progenitor Expansion, Biotechnology and Bioengineering (1994).

Priesner et al., Automated Enrichment, Transduction, and Expansion of Clinical-Scale CD62L+ T Cells for Manufacturing of Gene Therapy Medicinal Products, 27 Human Gene Therapy 10, 860-869 (2016).

Rosazza et al., Gene Electrotransfer: A Mechanistic Perspective, Current Gene Therapy (2016) ("Rosazza 2016").

Shi et al., "Performance of Mammalian Cell Culture Bioreactor with a New Impeller Design" Biotechnology and Bioengineering, vol. 40, pp. 260-270 (1992).

Stiff et al., Autologous transplantation of ex vivo expanded bone marrow cells grown from small aliquots after high-dose chemotherapy for breast cancer, Blood (2000) ("Stiff 2000").

Wang et al., Clinical Manufacturing of CAR T Cells: Foundation of a Promising Therapy, 3 Molecular Therapy—Oncolytics 1 (2016).

Wang et al., Manufacture of Tumor- and Virus-specific T Lymphocytes for Adoptive Cell Therapies, 22 Cancer Gene Therapy 2 (2015).

Zhang et al., Characterization of clinical grade CD19 chimeric antigen receptor T cells produced using automated CliniMACS Prodigy system, Drug Design, Development and Therapy (2018) ("Zhang 2018").

Zhu et al., Closed-system manufacturing of CD19 and dual-targeted CD20/19 chimeric antigen receptor T cells using the CliniMACS Prodigy device at an academic medical center, Cytotherapy (2018).

\* cited by examiner

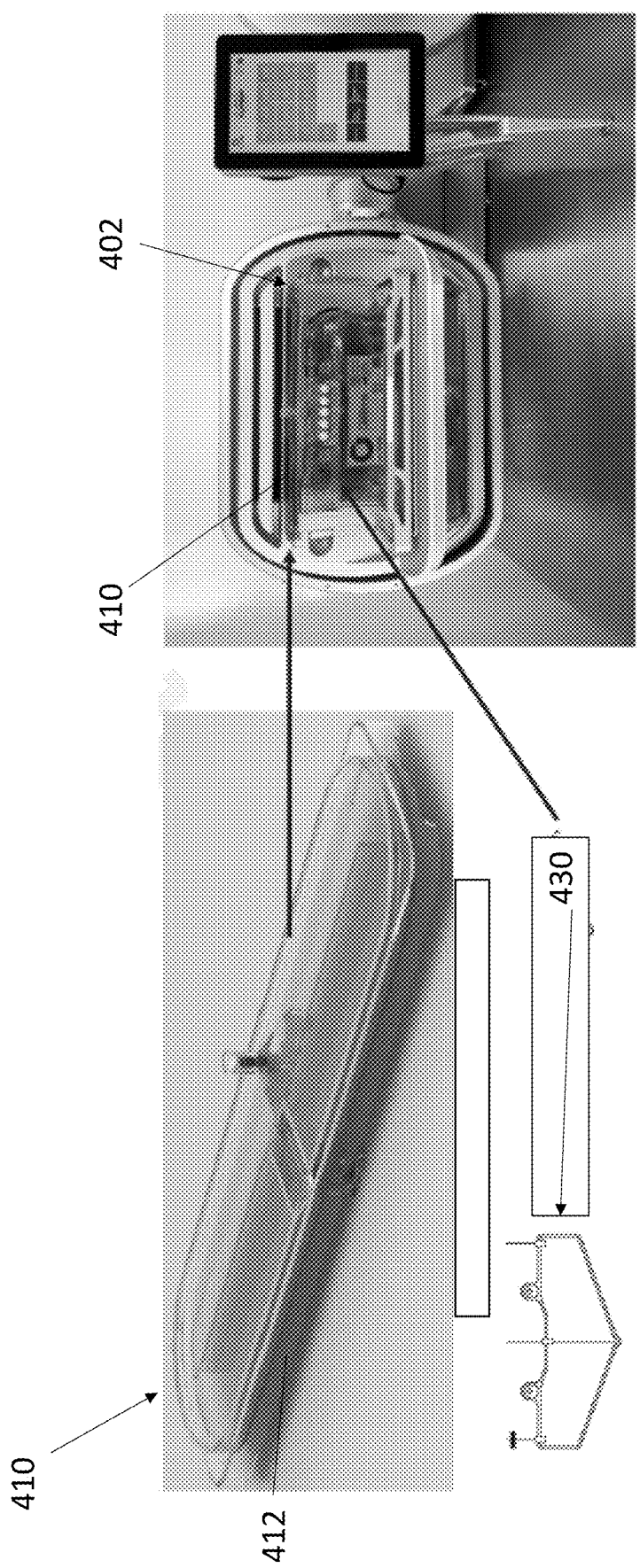

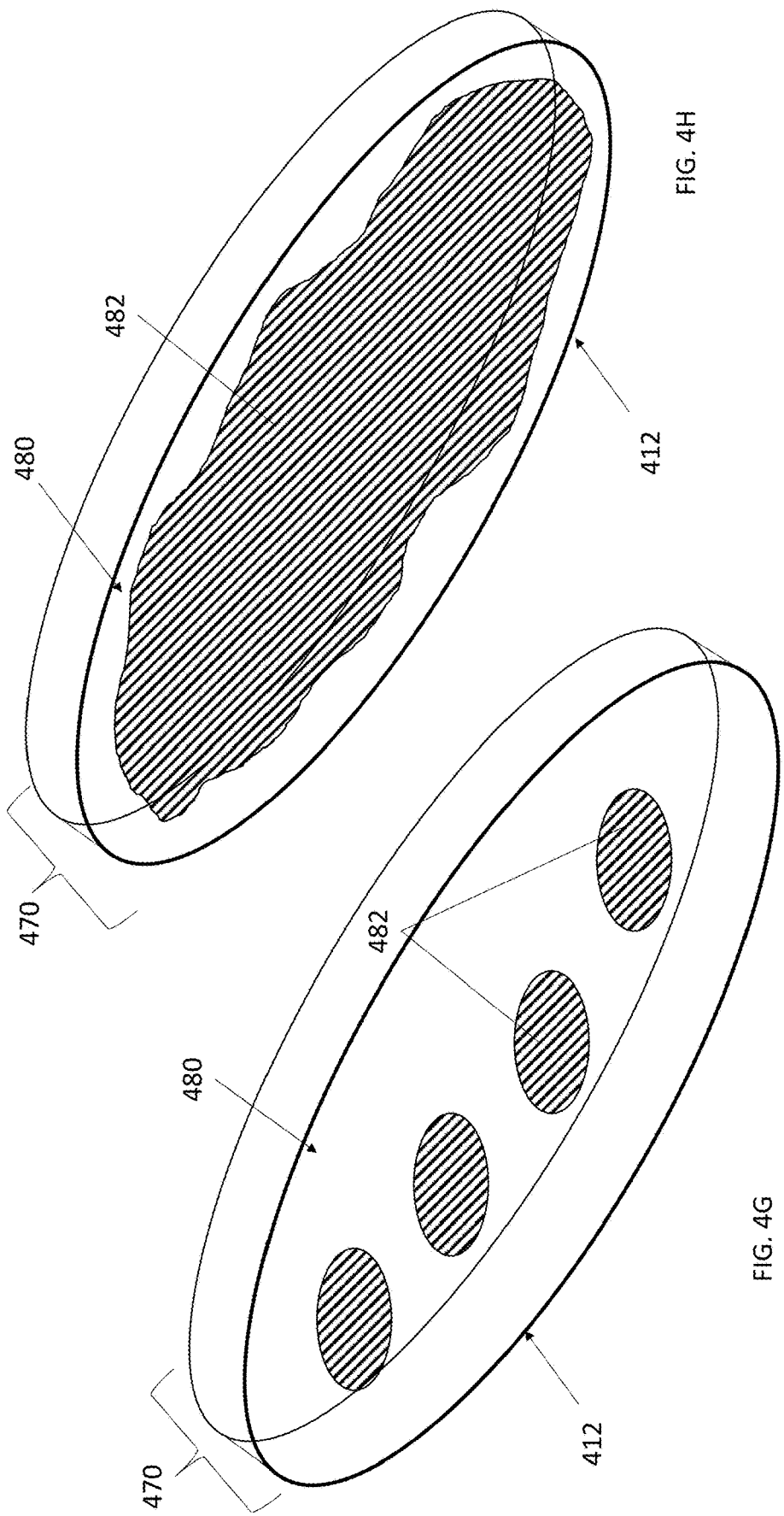

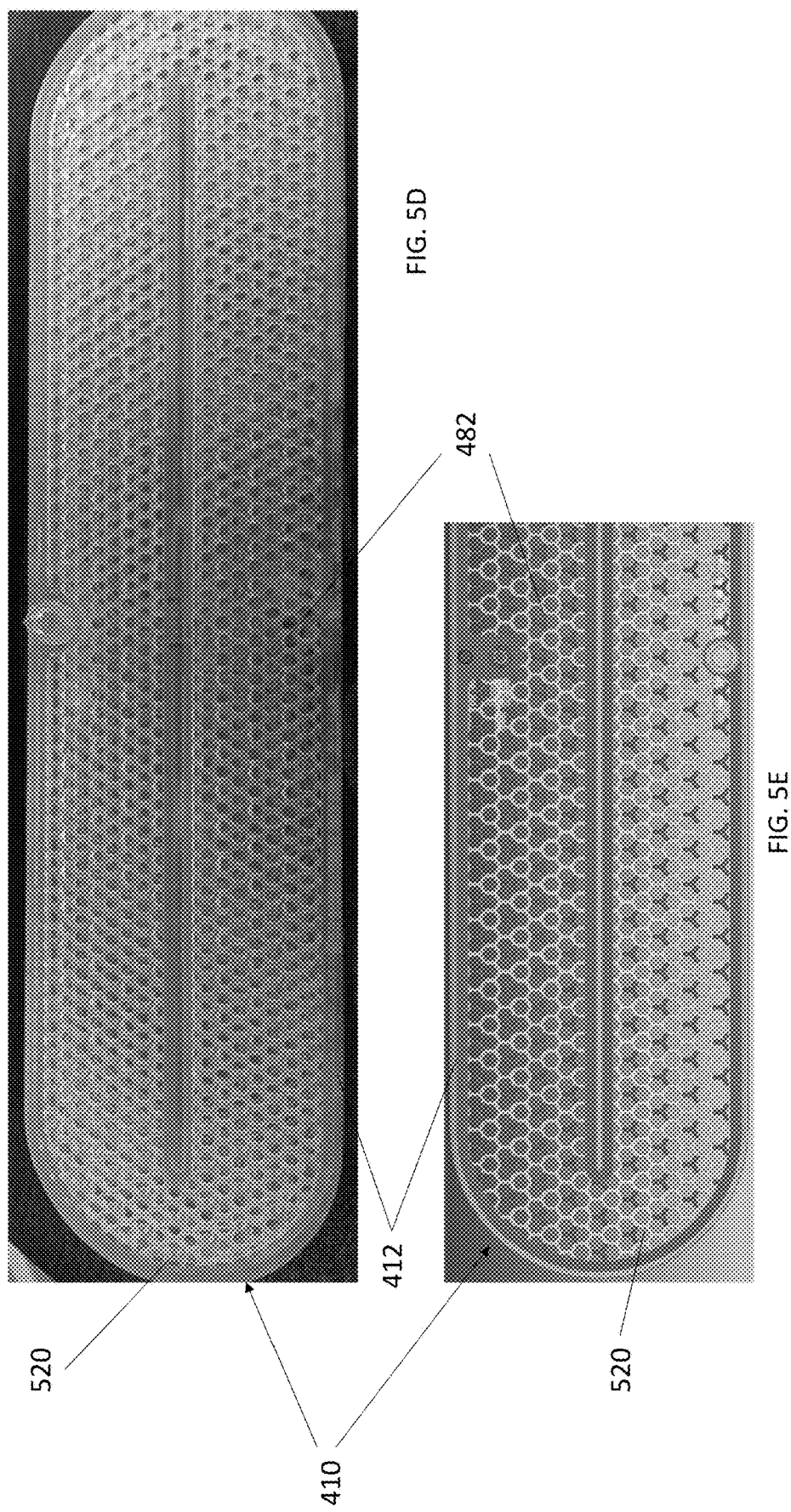

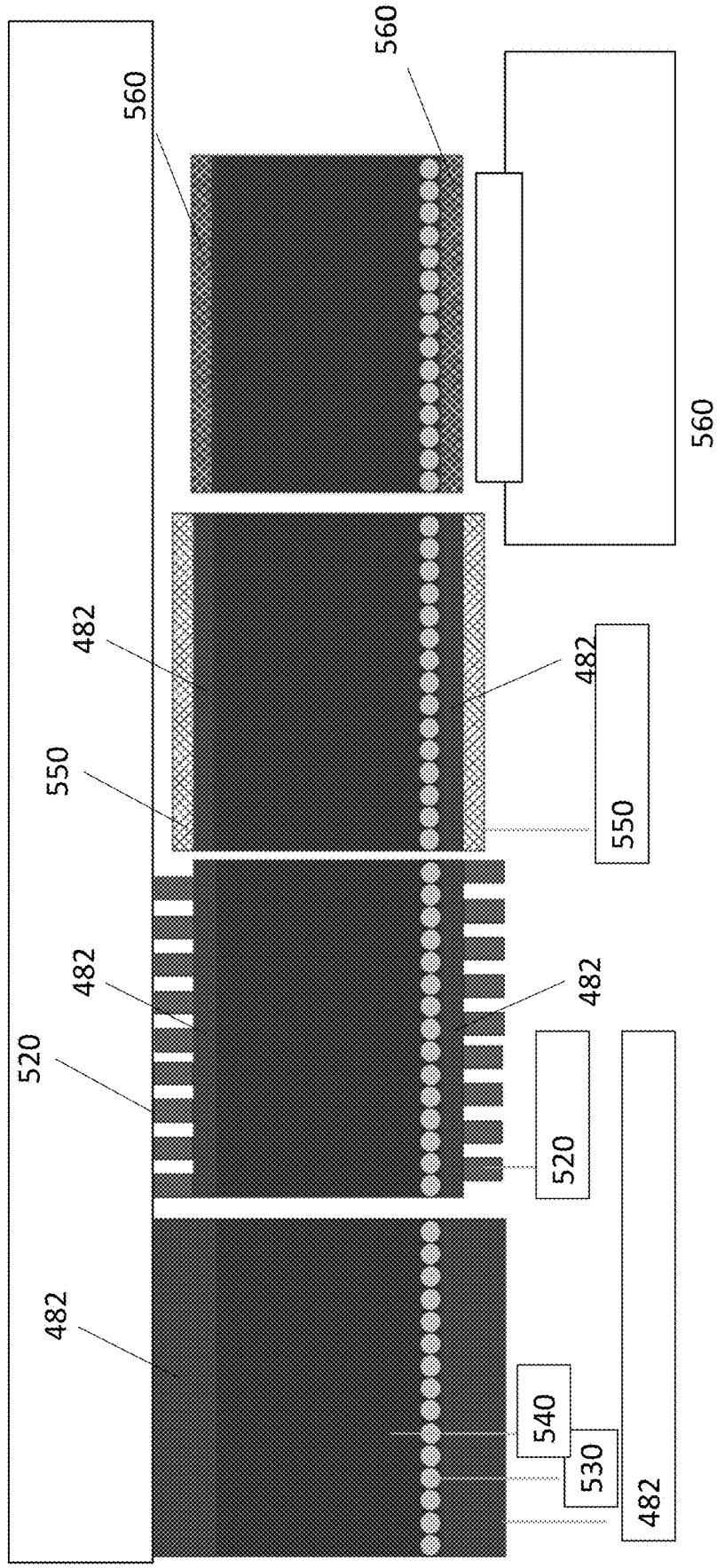

CELL CULTURE CHAMBER WITH IMPROVED CELL-CONTACTING SURFACES

CROSS-REFERENCE TO RELATED APPLICATIONS

The present application claims benefit of U.S. Provisional Patent Application No. 62/925,392, filed Oct. 24, 2019, the disclosure of which is incorporated by reference herein in its entirety.

FIELD OF THE INVENTION

The present disclosure provides cell culture chambers for use in automated cell engineering systems, and in particular, cell culture chambers that include improved cell-contacting surfaces. Improved cell-contacting surfaces can include a surface coating that promotes cell growth, adherence, differentiation, maintenance of phenotype, and/or improves transduction; a cell-contacting surface comprising a non-porous, gas-permeable material; as well as other modifications to the cell-contacting surfaces. Cassettes comprising the cell culture chambers are also provided.

BACKGROUND OF THE INVENTION

As anticipation builds about accelerated clinical adoption of advanced cell therapies, more attention is turning to the underlying manufacturing strategies that will allow these therapies to benefit patients worldwide. While cell therapies hold great promise clinically, high manufacturing costs relative to reimbursement present a formidable roadblock to commercialization. Thus, the need for cost effectiveness, process efficiency and product consistency is driving efforts for automation in numerous cell therapy fields, and particularly for T cell immunotherapies.

Integration of cell activation, transduction and expansion into a commercial manufacturing platform is critical for the translation of these important immunotherapies to the broad patient population. For these life-saving treatments to be applicable to the global patient population, a shift in manufacturing techniques must be implemented to support personalized medicine. The benefits of automation include labor time savings associated with using automation as well as improved product consistency, decreased room classification, decreased clean room footprint, decreased training complexities, and improved scale-up and tracking logistics. Furthermore, software can be used to streamline the documentation processes by using automatically generated electronic batch records to provide a history of all processing equipment, reagents, patient identification, operator identification, in-process sensor data, etc.

What is needed to advance these therapies and automated systems are components of cell expansion systems, such as cell culture chambers, that increase cell output, or provide desired cellular characteristics. The present application fulfills these needs.

SUMMARY OF THE INVENTION

In some embodiments provided herein is a cell culture chamber for use in an automated cell engineering system, the cell culture chamber comprising: a flat and non-flexible chamber, having a low chamber height and a cell-contacting surface, wherein at least a portion of the cell-contacting surface comprises a non-porous, gas-permeable material.

In further embodiments, provided herein is a cell culture chamber for use in an automated cell engineering system, the cell culture chamber comprising: a flat and non-flexible chamber, having a chamber height of about 0.5 cm to about 4 cm, and a cell-contacting surface, wherein at least 50% of the cell-contacting surface comprises a non-porous, gas-permeable material comprising silicone, fluoroethylene polypropylene (FEP), or ethyl vinyl olefin (EVO), and wherein the cell culture chamber further comprises at least one of: a distal port configured to allow for the removal of air bubbles from the cell culture chamber and/or as a recirculation port; a medial port configured to function as a recirculation inlet port; and a proximal port configured to function as a drain port for cell removal.

Also provided herein is a cassette for use in an automated cell engineering system, comprising: a high temperature chamber for carrying out activation, transduction and/or expansion of a cell culture, the high temperature chamber including a cell culture chamber; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber, wherein the cell culture chamber is a flat and non-flexible chamber, having a low chamber height and a cell-contacting surface, and the cell culture chamber is maintained in a substantially planar orientation in the cassette, and wherein at least a portion of the cell-contacting surface comprises a non-porous, gas-permeable material.

In additional embodiments, provided herein is a cell culture chamber for use in an automated cell engineering system, comprising: a flat and non-flexible chamber, having a low chamber height; and a surface coating on the chamber selected from the group consisting of: a surface coating that activates a cell; a surface coating that modulates a biological pathway in a cell; a surface coating that enhances growth of a cell; a surface coating that improves adhesion of a cell; a surface coating that inhibits a cell; a surface coating that responds to media conditions; and a surface coating that has controlled solubility.

In further embodiments, provided herein is a cassette for use in an automated cell engineering system, comprising: a high temperature chamber for carrying out activation, transduction and/or expansion of a cell culture, the high temperature chamber including a cell culture chamber; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber, wherein the cell culture chamber is a flat and non-flexible chamber, having a low chamber height, and the cell culture chamber is maintained in a substantially planar orientation in the cassette, and wherein the cell culture chamber has a surface coating selected from the group consisting of: a surface coating that activates a cell; a surface coating that modulates a biological pathway in a cell; a surface coating that enhances growth of a cell; a surface coating that improves adhesion of a cell; a surface coating that inhibits a cell; a surface coating that responds to media conditions; and a surface coating that has controlled solubility.

Also provided herein is a cassette for use in an automated cell engineering system, comprising: a high temperature chamber for carrying out activation, transduction and/or expansion of a cell culture, the high temperature chamber including a cell culture chamber; wherein the cell culture chamber is a flat and non-flexible chamber, having a low chamber height, and the cell culture chamber is maintained in a substantially planar orientation in the cassette; one or more fluidics pathways connected to the cell culture chamber, wherein the fluidics pathways provide recirculation, removal of waste and homogenous gas exchange and distribution of nutrients to the cell culture chamber without disturbing cells within the cell culture chamber; and a fluidics pathway connected to the cell culture chamber configured to introduce a surface coating material to the cell culture chamber, the surface coating material selected from the group consisting of: a surface coating material that activates a cell; a surface coating material that modulates a biological pathway in a cell; a surface coating material that enhances growth of a cell; a surface coating material that improves adhesion of a cell; a surface coating material that inhibits a cell; a surface coating material that responds to media conditions; and a surface coating material that has controlled solubility.

BRIEF DESCRIPTION OF THE FIGURES

FIG. 4A shows an automated cell engineering system in the closed configuration. FIG. 4B shows a cassette that can be inserted into the automated cell engineering. FIG. 4C shows a automated cell engineering system in the open configuration.

FIGS. 4D-4E show the location and orientation of a cell culture chamber utilized in an automated cell engineering system.

FIGS. 4G-4H show exemplary cell-contacting surfaces in accordance with embodiments hereof.

FIGS. 5D-5E show still further cell culture chambers in accordance with embodiments hereof.

FIGS. 5F-5I show various manufacturing techniques that can be used to create a cell culture chamber that includes a non-porous, gas-permeable material.

DETAILED DESCRIPTION OF THE INVENTION

The production of genetically engineered cells, including CAR T cells, typically requires manual involvement due to the patient-specific product. Automation of CAR T cell culture has been particularly challenging due to the multiple sensitive unit operations, including cell activation, transduction, and expansion. Thus, described herein are automated methods of CAR T cell production utilizing a fully-enclosed cell engineering system, as well as components for use in such cell engineering systems, in particular, cell culture chambers.

Automated Cell Processing

For production of genetically engineered cells, including autologous cell treatments such as T cell therapy, the need for cost effectiveness, process efficiency, and product consistency is particularly acute, as manufacturing micro-lot (one patient per lot) batches lacks the economies of scale that allogeneic (multiple patients per lot) processes can exploit. The larger and more localized workforce and facilities required for micro-lots places considerable demands on logistics and GMP compliance for manual production, especially with respect to availability and training of staff. In addition, the potential for variability in technique between operators can pose an undesirable risk to consistently meeting release criteria and ensuring a safe and dependable product.

As described herein, installation and comprehensive validation of automated manufacturing provides a solution to these logistical and operational challenges. An important approach to introducing automation to a production process is identifying the key modular steps where the operator applies a physical or chemical change to the production material, termed "unit operations." In the case of cell manufacturing, this includes steps such as cell separation, genetic manipulation, proliferation, washing, concentration, and cell harvesting. Manufacturers often identify focal process bottlenecks as the immediate opportunities for introducing automation. This is reflected in the technical operation spectrum of the majority of commercially available bioreactors, which tend to focus on discrete process steps. Process challenges in cell manufacturing (from sterility maintenance to sample tracking) are addressed herein by end-to-end automation that generates consistent cellular outputs while ameliorating inevitable process variability. The methods described herein also provide simplification, and the associated electronic records aid in complying with GMP standards.

Figure 1:
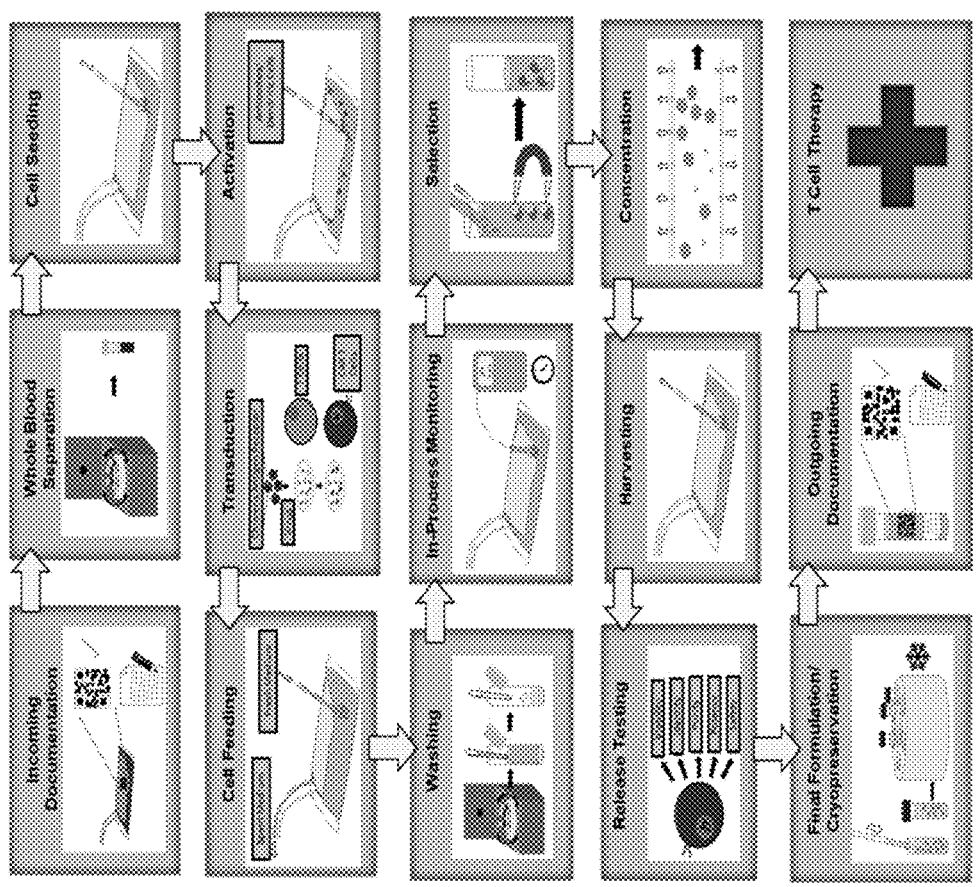
FIG. 1 shows a generalized manufacturing process for automated cell production, in particular, CAR-T production.

While specific protocols may vary for T cell manufacturing, a generalized chimeric antigen receptor T cell (CAR T) process is illustrated in FIG. 1. FIG. 1 describes unit operations of CAR T cell manufacturing, from initial processing of a patient blood sample to formulating output cells for autologous T cell therapy.

As described herein, to achieve cell manufacturing automation, the methods described herein provide for understanding the status of the cells at each transition point and how they are impacted by the specific unit operation. The micro-lot production for patient-specific therapies should be respectful of key process sensitivities that impact the feasibility of automation. Automation described herein successfully embraces various process steps.

Table 1 below highlights the challenges of some process steps identified for T cell automation and notes the impact of the sensitivity on the automation strategy. Note that for all unit operations, open transfer of cells between respective equipment is a key sensitivity due to the risk of contamination.

TABLE 1

Automation Challenges and Benefits

| Unit Operation | Challenges of Key Process Steps | Benefit of Automating |
|---|---|---|
| Fractionation | Highly variable based on donor cells and operator technique Residual impurities can impact performance | High purity of target starting population More consistent and improved product |
| Cell Seeding | Inhomogeneous cell distribution leads to variability in growth rates | Homogenous automated seeding strategy can improve consistency and potency |
| Activation | Stable contact between cells and activation reagent Uniform activation - homogeneous distribution | Automated loading can ensure reproducibly homogeneous distribution and activation which can be difficult to consistently achieve with manual methods |
| Transduction | Efficiency can be affected by the degree of cell-virus mixing, which may vary based on operator handling Increased exposure time may have negative impact on cells | Volume reduction prior to virus addition enables high degree of cell-virus contact Time-based operation enables cell transfer regardless of time of day Closed system decreases risk to operator |
| Electroporation | Efficiency can vary based on operator mixing, washing and concentration technique | Standardized protocols ensure consistent results when upstream and downstream steps are integrated |
| Feeding | Timing of media exchange needs to consider nutritional requirements based on cell growth, and the component stability at 37° C. | Biofeedback can optimize feeding schedule and minimize media use Components can be stored at refrigerated temperatures to prolong stability and automatically pre-warmed before use |
| Selection | Extensive handling steps can result in cell loss Operator variability | Full automation improves consistency |
| Harvest | Acellular materials (such as cell separation beads) to be removed prior to final formulation Manual pipetting variability can impact final yield | Cells automatically transferred from culture vessel regardless of time of day Improved final yield consistency over manual pipetting |
| Washing | Aggressive washing may induce shear stress or cause cell loss during supernatant removal | Gentle washing, filtration, or sedimentation without moving the culture vessels, can be utilized to reduce cell loss and remove residuals |
| Concentration | Cell recovery may vary by operator during aspiration | Automated volume reduction reduces operator variability Filtration methods also minimize cell loss |
| Formulation | Product must be well mixed Small working volumes magnify impact of volume inaccuracies Viability decreases with longer exposure times to cryopreservative | Automated mixing ensures homogenous distribution of cells in final formulation Automated volume addition removes risk of manual pipetting error or variability Increased automation reduces variability in temperature sensitive steps |

Tailoring the automation of a manual process around the sensitivities listed in Table 1 can support successful translation, maintenance or improvement on the performance of the cell therapy.

Figure 2:
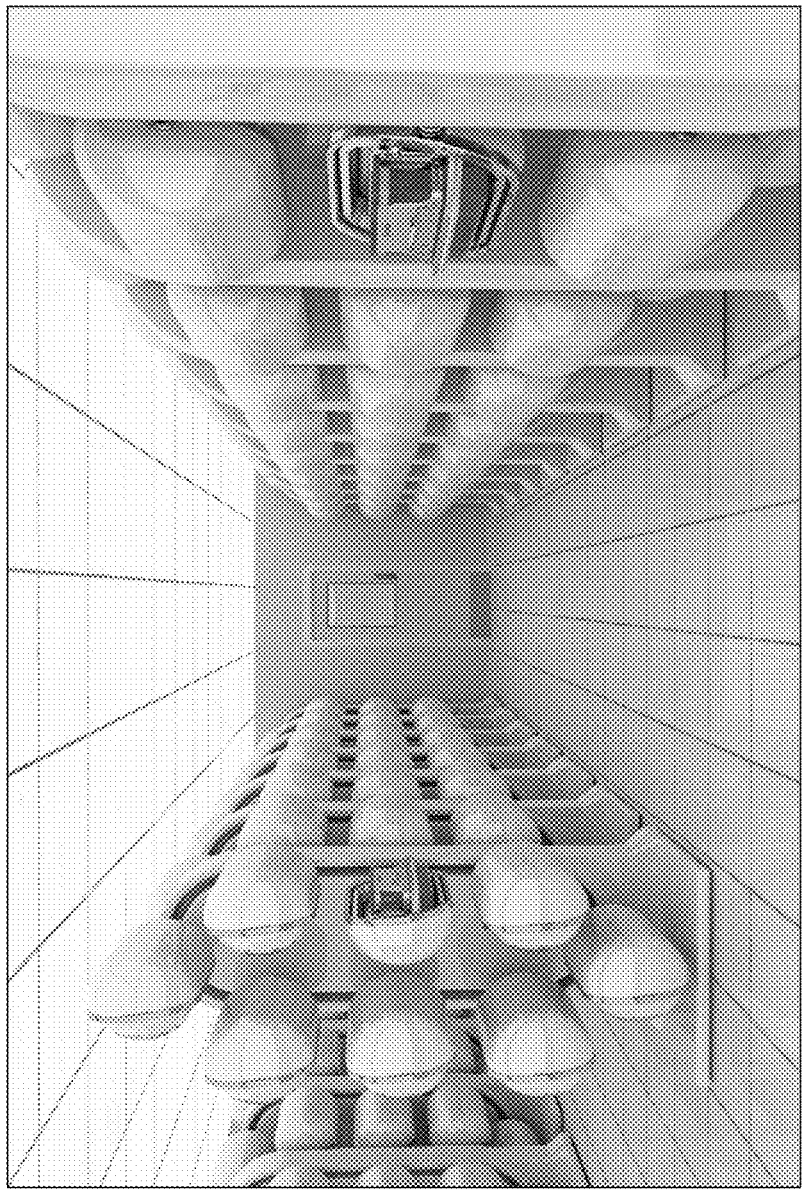
FIG. 2 shows a lab space containing exemplary automated cell engineering systems as described in embodiments herein.

A single all-in-one system can offer significantly greater space efficiency to minimize the required footprint in expensive GMP clean rooms. For example, as shown in FIG. 2, fully integrated automated systems are designed to maximize the required footprint to reduce expensive GMP clean room space. FIG. 2 shows 96 patient-specific end-to-end units running in a standard lab space.

Described herein are methods that are able to sense culture conditions and respond accordingly as a sophisticated bioreactor, by controlling factors such as physical agitation, pH, feeding, and gas handling. Furthermore, there are significantly different challenges with technology transfer related to autologous treatments compared to allogeneic treatments. Autologous products may have greater restrictions on stability between the manufacturing process and the patient treatment. Sites can be located globally rather than at a single center. Having a locked down (e.g., fully enclosed) all-in-one system significantly improves the technology transfer process between sites.

As described herein, in embodiments, the methods and components described herein utilize the COCOON platform (Octane Biotech (Kingston, ON)), which integrates multiple unit operations in a single turnkey platform (see e.g., U.S. Published Patent Application No. 2019/0169572, the disclosure of which is incorporated by reference herein in its entirety). It is understood, however, that other fully or partially automated cell culture apparatus may be used according to embodiments hereof, including those commercially available such as PRODIGY available from Miltenyi Biotech, Inc., XURI and SEFIA from General Electric Healthcare, and systems available from Atvio Biotech Ltd.

Figure 3:
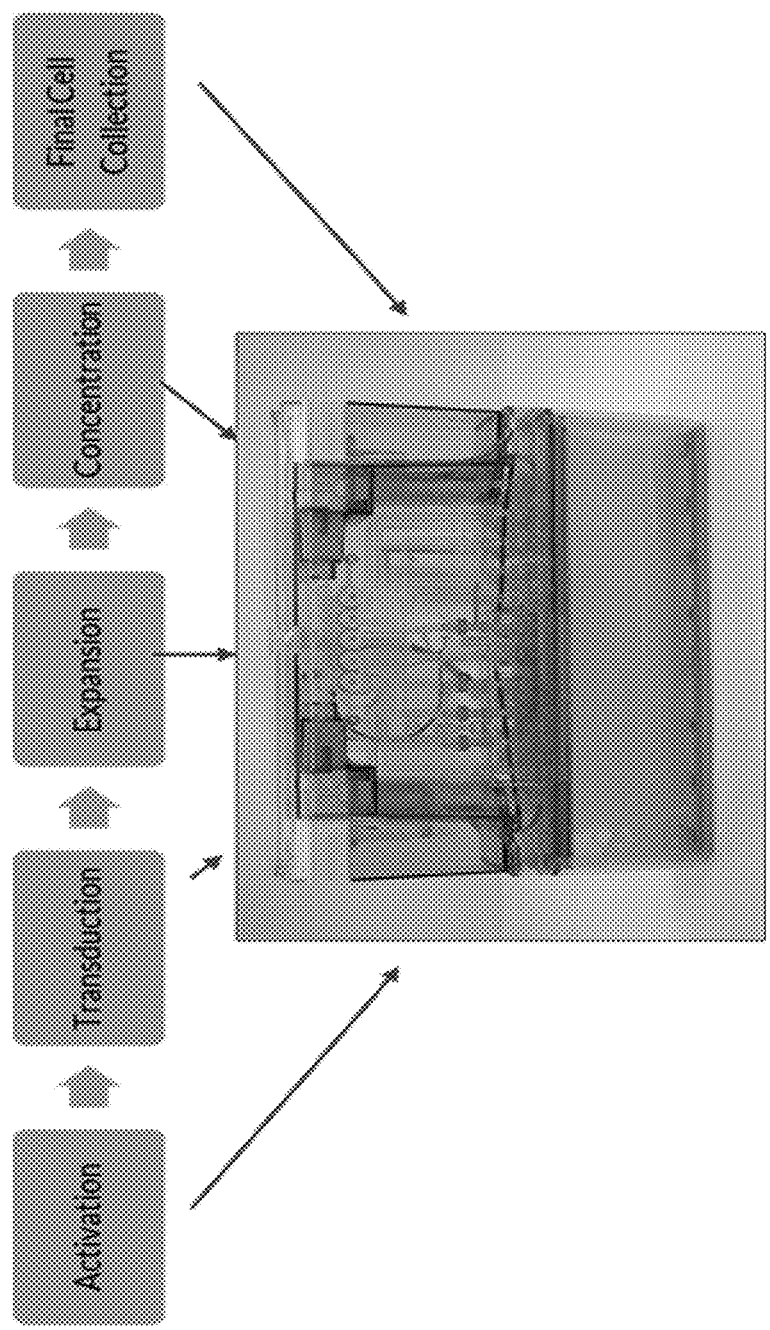
FIG. 3 shows a cell production process that can be performed in a cell engineering system as described in embodiments herein.

The methods and devices described herein have been used to expand CAR T cells (including activation, viral transduction and expansion, concentration and washing) in a fully-integrated closed automation system (FIG. 3).

In exemplary embodiments, the methods and systems described herein produce at least about 50 million viable genetically modified immune cells. In suitable embodiments, the methods described produce at least about 100 million viable genetically modified immune cells, or at least about 200 million cells, at least about 300 million cells, at least about 400 million cells, at least about 500 million cells, at least about 600 million cells, at least about 700 million cells, at least about 800 million cells, at least about 1 billion cells, at least about 1.1 billion cells, at least about 1.2 billion cells, at least about 1.3 billion cells, at least about 1.4 billion cells, at least about 1.5 billion cells, at least about 1.6 billion cells, at least about 1.7 billion cells, at least about 1.8 billion cells, at least about 1.9 billion cells, at least about 2 billion cells, least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, at least about 3.0 billion, at least about 4.0 billion, at least about 5.0 billion, at least about 6.0 billion, at least about 7.0 billion, at least about 8.0 billion, at least about 9.0 billion, at least about 10.0 billion, at least about 11.0 billion, at least about 12.0 billion, at least about 13.0 billion, at least about 14.0 billion, at least about 15.0 billion, at least about 16.0 billion, at least about 17.0 billion, at least about 18.0 billion, at least about 19.0 billion, at least about 20.0 billion, at least about 21.0 billion, at least about 22.0 billion, at least about 23.0 billion, at least about 24.0 billion, at least about 25.0 billion, at least about 26.0 billion, at least about 27.0 billion, at least about 28.0 billion, at least about 29.0 billion, at least about 30.0 billion, at least about 5-10 billion, at least about 10-15 billion, at least about 15-20 billion, at least about 20-25 billion, at least about 25-30 billion, or at least about 20-30 billion genetically modified immune cells.

The methods and systems described herein can also be used in the production of stem cells, including a pluripotent stem cell, a hematopoietic stem cell or a mesenchymal stem cell. In exemplary embodiments, the methods and systems described herein produce at least about 50 million viable stem cells. In suitable embodiments, the methods described produce at least about 100 million viable stem cells, or at least about 200 million cells, at least about 300 million cells, at least about 400 million cells, at least about 500 million cells, at least about 600 million cells, at least about 700 million cells, at least about 800 million cells, at least about 1 billion cells, at least about 1.1 billion cells, at least about 1.2 billion cells, at least about 1.3 billion cells, at least about 1.4 billion cells, at least about 1.5 billion cells, at least about 1.6 billion cells, at least about 1.7 billion cells, at least about 1.8 billion cells, at least about 1.9 billion cells, at least about 2 billion cells, least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, or at least about 3.0 billion stem cells.

Cell Engineering Systems

Described herein are components of a fully enclosed cell engineering system 400 (also called automated cell engineering system) (see FIGS. 4A, 4B), suitably having instructions thereon for performing activating, transducing, expanding, concentrating, and harvesting steps. Cell engineering systems for automated production of genetically modified immune cells, including CAR T cells, are described herein, and are also called automated cell engineering system, COCOON, or COCOON system throughout. For example, a user can provide a cell engineering system pre-filled with a cell culture and reagents (e.g., an activation reagent, a vector, cell culture media, nutrients, selection reagent, and the like) and parameters for the cell production (e.g., starting number of cells, type of media, type of activation reagent, type of vector, number of cells or doses to be produced, and the like), the cell engineering system is able to carry out the methods of producing various cells, including stem cells, and genetically modified immune cell cultures, including CAR T cells, without further input from the user. At the end of the automated production process, the cell engineering system may alert the user (e.g., by playing an alert message or sending a mobile app alert) for collecting the produced cells. In some embodiments, the fully enclosed cell engineering system includes sterile cell culture chambers. In some embodiments, the fully enclosed cell engineering system minimizes contamination of the cell cultures by reducing exposure of the cell culture to non-sterile environments. In additional embodiments, the fully enclosed cell engineering system minimizes contamination of the cell cultures by reducing user handling of the cells.

As described herein, the cell engineering systems suitably include a cassette 402. Thus, in embodiments, provided herein is a cassette for use in an automated cell engineering system. As used herein a "cassette" refers to a largely self-contained, removable and replaceable element of a cell engineering system that includes one or more chambers for carrying out the various elements of the methods described herein, and suitably also includes one or more of a cell media, an activation reagent, a vector, etc.

Figure 4B:
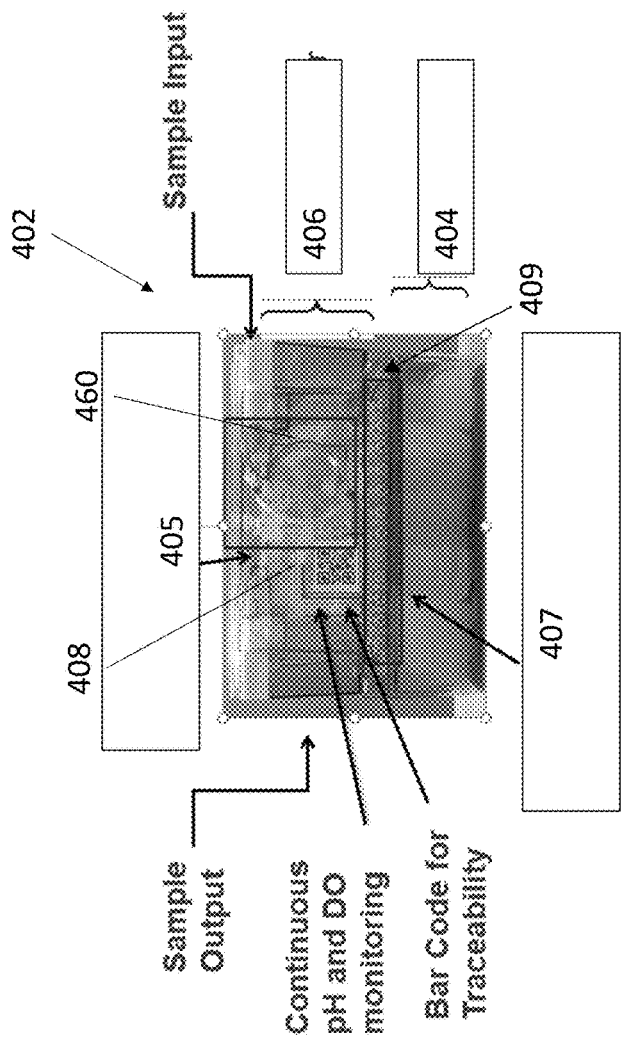
FIGS. 4A-4C show an overview of an automated cell engineering system.
Figure 4A:
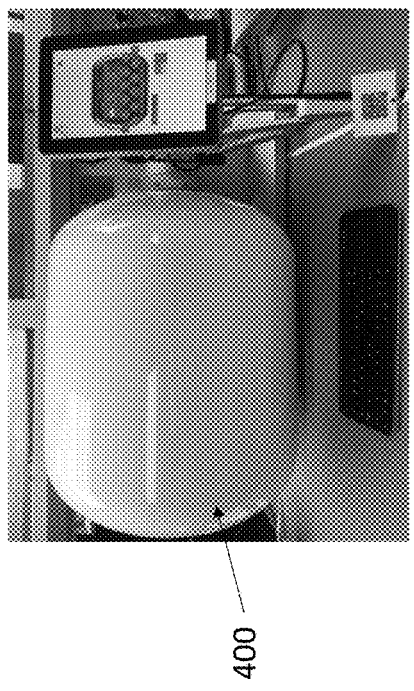
Figure 4C:
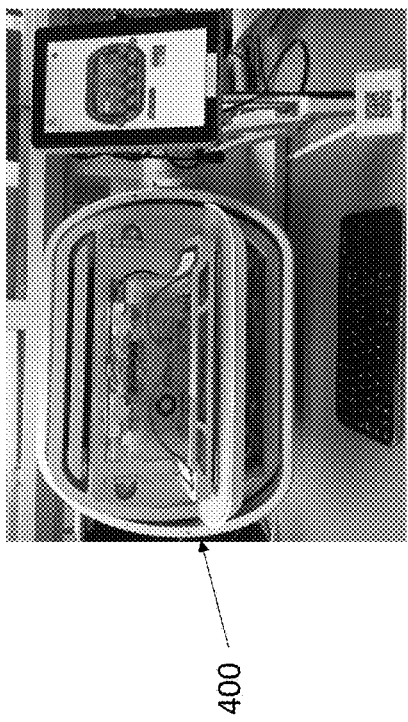

FIG. 4B shows an embodiment of a cassette 402 in accordance with embodiments hereof. In embodiments, cassette 402 optionally includes a low temperature chamber 404, for storage of a cell culture media, and suitably includes a high temperature chamber 406, for carrying out activation, transduction and/or expansion of an immune cell culture. Suitably, high temperature chamber 406 is separated from low temperature chamber 404 by a thermal barrier 409. As used herein "low temperature chamber" refers to a chamber, suitably maintained below room temperature, and more suitably from about 4° C. to about 8° C., for maintenance of cell media, etc., at a refrigerated temperature. The low temperature chamber can include a bag or other holder for media, including about 1 L, about 2 L, about 3 L, about 4 L, or about 5 L of fluid. Additional media bags or other fluid sources can be connected externally to the cassette, and connected to the cassette via an access port.

As used herein "high temperature chamber" refers to chamber, suitably maintained above room temperature, and more suitably maintained at a temperature to allow for cell proliferation and growth, i.e., between about 35-40° C., and more suitably about 37° C.

In embodiments, high temperature chamber 406 suitably includes a cell culture chamber 410 (also called proliferation chamber or cell proliferation chamber throughout), as shown in FIG. 4D and FIG. 4E.

The cassettes further include one or more fluidics pathways connected to the cell culture chamber, wherein the fluidics pathways (408 within cartridge 402 of FIG. 4B) provide recirculation, removal of waste and homogenous gas exchange and distribution of nutrients to the cell culture chamber without disturbing cells within the cell culture chamber. Cassette 402 also further includes one or more pumps 405, including peristaltic pumps, for driving fluid through the cassette, as described herein, as well as one or more valves 407, for controlling the flow through the various fluidic pathways.

In exemplary embodiments, as shown in FIG. 4D, cell culture chamber 410 is flat and non-flexible chamber 470 (i.e., made of a substantially non-flexible material such as a plastic) that does not readily bend or flex. The use of a non-flexible chamber allows the cells to be maintained in a substantially undisturbed state. As shown in FIG. 4E, cell culture chamber 410 is oriented so as to allow the cell culture (suitably an immune cell culture) to spread across the bottom 412 of the cell culture chamber. As shown in FIG. 4E, cell culture chamber 410 is suitably maintained in a position that is substantially planar, i.e., parallel with the floor or table, maintaining the cell culture in an undisturbed state, allowing the cell culture to spread across a large area of the bottom 412 of the cell culture chamber. As used herein "flat" with regard to the cell culture chamber means that the bottom 412 (as well as the top and sides) of the chamber has less than about 5° bow or warp in the shape of the chamber (from a completely flat surface or plane), suitably about 0° to about 4°, or about 3°. This slight warp allows for uniform seeding and growth of cells on the bottom 412, but provides enough of an angle to allow air bubbles to rise to the highest point and be removed.

In embodiments, the overall thickness of cell culture chamber 410 (i.e., the chamber height 442) is low, on the order of about 0.5 cm to about 5 cm. Suitably, the cell culture chamber has a volume of between about 0.50 ml and about 500 ml, about 0.50 ml and about 300 ml, more suitably between about 50 ml and about 200 ml, or the cell culture chamber has a volume of about 180 ml. Larger cell culture chamber volumes on the order of 1-2 L or more can also be used. The use of a low chamber height 442 (less than 5 cm, suitably less than 4 cm, less than 3 cm, or less then 2 cm, or about 0.5 cm to about 4 cm, about 0.5 cm to about 3 cm, about 0.5 cm to about 2 cm, or about 1 cm to about 2 cm, or about 1 cm to about 3 cm, or about 2 cm to about 3 cm) allows for effective media and gas exchange in close proximity to the cells. Ports are configured to allow mixing via recirculation of the fluid without disturbing the cells. Larger height static vessels can produce concentration gradients, causing the area near the cells to be limited in oxygen and fresh nutrients. Through controlled flow dynamics, media exchanges can be performed without cell disturbance. Media can be removed from the additional chambers (no cells present) without risk of cell loss.

In embodiments, provided herein is a cell culture chamber 410 for use in an automated cell engineering system 400, comprising: a flat and non-flexible chamber 470, having a low chamber height 442; and a cell-contacting surface 480, wherein at least a portion of the cell-contacting surface comprises a non-porous, gas-permeable material 482.

In exemplary embodiments, the cell-contacting surface 480 refers to the bottom 412 of the cell culture chamber 410. However, "cell-contacting surface" can also include additional elements within cell culture chamber 410, for example various scaffolds, supports, growth platforms, etc. "Cell-contacting surface" can also refer to one or more sides 416 of the cell culture chamber 410. The cell engineering systems 400 described herein have the ability to tilt and rotate the cell culture chamber 410, during which additional components of the chamber can become cell-contacting surfaces as the cells move within the chamber. The cell-contacting surface can also include multiple structures cut or made into the surface, generating channels, waves or other structures to add surface area to increase cell adhesion.

In further embodiments, a non-cell-contacting surface of culture chamber 410 can also comprise a non-porous, gas-permeable material 482. Suitably, in addition the bottom 412 of cell culture chamber 410 comprising a non-porous, gas-permeable material 482, top 414 of cell culture chamber 410 also comprises a non-porous, gas-permeable material 482.

As used herein, "a non-porous, gas-permeable material" means any composition, film, or material used for gas-permeable cell culture devices, that allows for gases to pass and enter cell culture chamber 410, but which does not contain pores or holes that allow for passage or leakage of liquids (e.g., cell media). Exemplary non-porous, gas-permeable materials include, but are not limited to, silicone, fluoroethylene polypropylene (FEP), polyolefin, ethyl vinyl olefin (EVO) and ethylene vinyl acetate copolymer. Non-porous, gas-permeable materials as described herein suitably help to deliver one or more gasses, including oxygen, nitrogen, $CO_2$, etc., to the cells in the cell culture chamber 410.

In embodiments, non-porous, gas-permeable material 482 does not allow water evaporation from the cell culture chamber 410. This can be accomplished either by selection of an appropriate material that limits or eliminates water evaporation, or through the use of a water layer that sits on top of a cell culture media within the cell culture chamber 410, but below a gas-permeable material 482 that is included in the top 414 of the cell culture chamber 410. In other embodiments, two or more different gas-permeable materials 482 can be utilized, one on a top 414 of the cell culture chamber 410, and a different material on the bottom 412.

In exemplary embodiments, "a portion" of the cell-contacting surface 480, or a non-cell-contacting surface such as top 414, comprises the non-porous, gas-permeable material. As used herein, "a portion" refers to at least about 20% of the cell-contacting surface, or non-cell-contacting surface being made up of the non-porous, gas-permeable material. That is, at least about 20% of the surface that is designed to be cell-contacting (suitably the bottom 412 of the cell culture chamber) or other scaffold, support or structure, or a non-cell contacting surface such as top 414, is made from the non-porous, gas-permeable material as the primary structural component of the surface. In such embodiments in which less than 100% of the cell-contacting surface is made of the non-porous, gas-permeable material, the remainder of the cell-contacting surface can include other suitable materials, including various plastics that promote the adhesion and growth of cells (e.g., polypropylene, polystyrol, polystyrene, etc.). In embodiments in which less than 100% of the non-cell-contacting surface is made of the non-porous, gas-permeable material, the remainder of the non-cell-contacting surface can include other suitable materials, including various plastics that provide structural support (e.g., polypropylene, polystyrol, polystyrene, etc.).

In embodiments, at least about 30% of the cell-contacting surface is made up of the non-porous, gas-permeable material, more suitably at least about 40%, at least about 50%, at least about 60%, at least about 70%, at least about 80%, at least about 90%, or at least about 100% (i.e., the entirety) of the cell-contacting surface comprises the non-porous, gas-permeable material.

In embodiments, at least about 30% of the non-cell-contacting surface is made up of the non-porous, gas-permeable material, more suitably at least about 40%, at least about 50%, at least about 60%, at least about 70%, at least about 80%, at least about 90%, or at least about 100% (i.e., the entirety) of the non-cell-contacting surface comprises the non-porous, gas-permeable material.

FIGS. 4G-4H show schematic exemplary structures in which less than the entire cell-contacting surface (in this case, bottom 412 of cell culture chamber 410), comprises the non-porous gas-permeable material. In such embodiments, the cell culture chamber includes a cell-contacting surface 480 that comprises a plurality of separate sections, each section comprising the non-porous, gas-permeable material 482. For example, holes or separate sections of the cell-contacting surface 480 can include the non-porous gas-permeable material 482, while other portions of bottom 412 comprise other suitable materials, including various plastics that promote the adhesion and growth of cells. These holes or sections can be regular in shape, or irregular, and can be of any size or number, depending on the desired coverage of cell-contacting surface 480 with the non-porous gas-permeable material 482. Chamber 470 is represented as a cylindrical shape, but other shapes can readily be envisioned, and the shape in FIGS. 4G-4H is provided for illustrative purposes.

In further embodiments one or more sides of cell culture chamber 410 can be provided with at least some portion comprising a non-porous, gas-permeable material 482.

In still further embodiments, additional components of cassette 402, including for example pumps 405, valves 407 and fluidics pathways 408 can also include a non-porous, gas-permeable material 482 that can aid in transferring gas to the cells as they pass through the cassette 402.

Silicone as used herein, is a synthetic polymer made of repeating units of siloxane, combined with carbon, hydrogen and sometimes other elements. As described in detail herein, the use of silicone as the non-porous, gas-permeable material in the cell culture chambers provides increased gas exchange. Silicone has excellent oxygen permeability, can allow for optical observation, is not easily punctured, and can be easily fabricated into a wide variety of shapes.

In exemplary embodiments, the thickness of the non-porous, gas-permeable material is less than about 0.5 inches, more suitably less than about 0.2 inches, less than about 0.1 inches, less than about 0.05 inches, or about 0.010-0.050 inches, about 0.010 inches, about 0.020 inches, about 0.030 inches, about 0.040 inches or about 0.050 inches.

In further embodiments, the non-porous, gas-permeable material can be stretched to make it thinner, thereby increasing the gas exchange through the material. This stretching can be carried out prior to integration into the structure of the cell culture chamber 410, or the material can be placed under tension in the preparation of the cell culture chamber 410 or during the inclusion of the material in the cell culture chamber, so that the non-porous, gas-permeable material is stretched.

Exemplary sources of silicone and silicone-based materials include, TEFLON® as well as, WO 01/92462, U.S. Pat. Nos. 4,939,151, 6,297,046, and 9,255,243, the disclosures of each of which are incorporated by reference herein in their entireties.

In exemplary embodiments, a cell-contacting surface can further include a surface coating on the surface selected from the group consisting of: a surface coating that activates a cell; a surface coating that modulates a biological pathway in a cell; a surface coating that enhances growth of a cell; a surface coating that increases transduction efficiency of a cell; a surface coating that improves selection for a certain type of cells; a surface coating that improves adhesion of a cell; a surface coating that inhibits a cell; a surface coating that responds to media conditions (for example a color change as a monitoring aid); and a surface coating that has controlled solubility (for example, to attain controlled release of coating contents). Thus, in embodiments, the non-porous gas-permeable material that suitably makes up a portion or the entirety of the cell-contacting surface can further include a surface coating as described herein. In other embodiments, the remainder of the cell-contacting surface that does not include a non-porous gas-permeable material can also include a surface coating as described herein. In other embodiments, the entire cell-contact surface does not include a non-porous gas-permeable material, but still includes a surface coating as described herein. The adhesion of a cell can also provide an opportunity for cell selection to promote the growth of a desired population, while not allowing adherence of an undesired population.

As used herein a "surface coating" refers to a material that forms a film, a layer, or a covering on one or more surfaces of a cell culture chamber 410. Methods for applying a surface coating to the surfaces of a cell culture chamber can include, for example, painting, dip-coating, layering, flowing, spraying, deposition methods including spin-coating, etc.

In exemplary embodiments, the surface coating is provided on the bottom 412 of the cell culture chamber 410, suitably including the cell-contacting surface 480 and the non-porous, gas-permeable material 482. However, the surface coating can also be provided on top 414 and/or sides 416 of the cell culture chamber (see FIG. 4F).

As used herein, a "surface coating that activates a cell" refers to a material, substrate or component that causes a cell to proliferate and/or differentiate.

As used herein, a "a surface coating that modulates a biological pathway in a cell" refers to a material, substrate or component that causes one or more actions among molecules in a cell, resulting in a certain product or change in the cell. For example, such surface coatings can trigger the assembly of new molecules, such as a fat or protein, turn genes on and off, or cause a cell to move.

As used herein, "a surface coating that enhances growth of a cell" refers to a material, substrate or component that causes the cell to grow faster or in a greater number, than in the absence of the material.

As used herein, "a surface coating that improves adhesion of a cell" refers to a material, substrate or component that causes the cell to better interact with and attach to a surface, and also interact with other cells, as they adhere to a surface.

As used herein, "a surface coating that inhibits a cell" refers to a material, substrate or component that causes the cell to not grow and/or not adhere to a cell-contacting surface.

As used herein "a surface coating that responds to media conditions" refers to a material, substrate or component that changes when a media condition changes. Exemplary changes include changes in temperature, pH, oxygen level or concentration, level of toxic gases, presence of toxic substances, and include for example a color change as a monitoring aid.

As used herein "a surface coating that has controlled solubility" refers to a material, substrate or component that releases from the surface at a particular time or in response to a particular temperature or pH, for example, to attain controlled release of coating contents.

A surface treatment (e.g. corona, plasma, etching, etc) can be used to facilitate the binding (or rejection) of a coating. This can allow for selective surface modifications to enable two different types of cells to be grown in the same cell culture chamber, or for selective unit operations within the same chamber.

Exemplary surface coatings that can be applied to one or more surfaces of the cell culture chamber, include but are not limited to, polycationic reagents (polybrene, protamine sulphate, poly-L-lysine, peptides with a net positive charge, amphipathic cationic peptides), poloxamers, adhesion molecules such as fibronectin or modified fibronectin (RETRONECTIN®), protein targeting domains such as antibodies, antibody complexes, nucleic acids (including DNA and RNA), poly lactic acid, polyvinylalcohols, polysaccharides or dextrans or derivatives thereof, collagen types (I to VIII), polyethylene glycol (PEG), fibrin, vitronectin, laminin, elastin, gelatin, hyaluronic acid, keratan sulfate, chondroitin sulfate, heparan sulfate proteoglycans, poly-d-lysine, avidin, streptavidin, biotin, antibodies against biotin or protein tags, protein tags like Ilsopeptag, BCCP, Myc-tag, Calmodulin-tag, FLAG-tag, HA-tag, His-tag, Maltose binding protein-tag, Nus-tag, Glutathione-S-transferase-tag. Green fluorescent protein-tag, Thioredoxin-tag, S-tag, Softag 1, Softag 3, Strep-tag, SBP-tag, Ty tag, certia, poly lactate, polyvinyl alcohols, polysaccharides and dextran.

Additional surface coatings can include diagnostic agents that undergo a change in color or emission/fluorescence upon binding to a particular cell type or cell surface receptor. In such embodiments, the surface coatings can act as a signal that a cell has reached a desired stage, or that the cells have reached a desired confluence or other characteristic.

In additional embodiments, a "surface treatment" can also be utilized on one or more surfaces of the cell culture chamber 410, and/or one or more surfaces within the cartridge 402 that contact the cells, including for example pumps 405, valves 407 and fluidics pathways 408, and can also be applied to a non-porous, gas-permeable material 482. Exemplary surface treatments include chemical treatments, etching, micro-etching, electrochemical treatments, etc. Additional surface treatments include corona or gas plasma treatment to alter the surface structure of a cell culture chamber, including a cell-contacting surface such as a polystyrene surface. Exemplary gas plasma treatments include the use of air, argon, nitrogen, oxygen, amine, etc., to cause a desired functional group on the surfaces of the cell culture chamber. These surface treatments can result in a change in the hydrophobicity of the surface, and cause a change in a range of biological effects, including an increase in activation, an increase in transduction efficiency, an increase or decrease in cellular attachment, accelerated proliferation, selection for certain cell types, prevention or increase of cell adhesion, change of cell biological pathways, cell differentiation, supporting or rejecting the binding of proteins, etc.

In addition, gas plasma treatments can be used to increase the ability of a non-porous, gas-permeable material 482 to adhere, to be glued, or otherwise to be attached, to a surface, such as the bottom 412 or top 414 or cell culture chamber 410, or other surface including polystyrene surfaces. As many non-porous, gas-permeable materials 482 may be hydrophobic, adhering them to a hard surface, such as polystyrene, with a glue or other adhesive can be difficult. Plasma oxidation of both the cell culture chamber 410 and the non-porous, gas-permeable materials 482, increases the surface energy of both of the structures. As a return to hydrophobic characteristics can happen quickly, it is desirable to quickly adhere, e.g., glue, the non-porous, gas-permeable materials 482 to the cell culture chamber 410, so as to achieve a solid bond and lasting structural integrity.

A discussion of micro-etching and nano-etching on the behavior of cells in a cell culture environment is provided, for example, in Martinez, et al., "Effects of artificial micro- and nano-structure surfaces on cell behaviour," *Annals of Anatomy* 191:126-135 (2009), the disclosure of which is incorporated by reference herein in its entirety.

The non-porous, gas-permeable material 482 can also be cast onto or into a material, such as cell culture chamber 410, to provide the gas-permeable characteristics described herein. Casting of the non-porous, gas-permeable membrane material 482 can be carried out by various methods known in the art. By casting the non-porous, gas-permeable membrane material 482 onto or into a cell culture chamber 410, such as plastic, polystyrene, chamber, the structural strength and integrity of the gas-permeable membrane can also be increased, while still maintaining the gas-permeable characteristics.

In other embodiments, the non-porous, gas-permeable material 482 can be infused into the material, such as cell culture chamber 410, to provide the gas-permeable characteristics described herein. Infusing the non-porous, gas-permeable membrane material 482 into the cell culture chamber can be carried out by various methods known in the art. By infusing the non-porous, gas-permeable membrane material 482 into a cell culture chamber 410, such as plastic, polystyrene, chamber, the structural strength and integrity of the gas-permeable membrane can also be increased, while still maintaining the gas-permeable characteristics.

As described herein, the surface coatings, or surface treatment described herein, suitably activate, modulate a biological pathway, enhance growth, or improve adhesion of an immune cell (e.g., a T cell), and in embodiments, a stem cell or a progenitor cell. In suitable embodiments, the stem cell is a pluripotent stem cell, a hematopoietic stem cell or a mesenchymal stem cell. In additional embodiments, cells that can be grown in the automated cell engineering systems described herein and utilizing the described methods include connective tissue cells, cardiac cells, retinal cells, muscle cells, skin cells, etc.

Figure 4F:
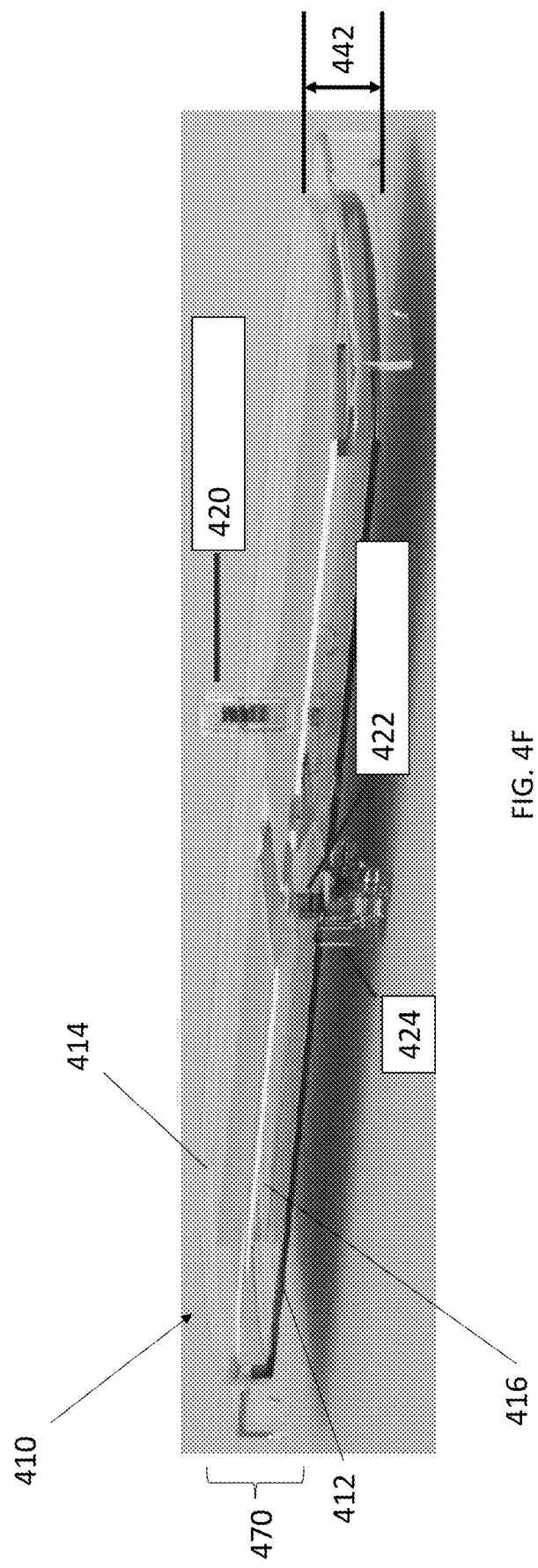
FIG. 4F shows a more detailed view of the cell culture chamber utilized in an automated cell engineering system.

In exemplary embodiments, as shown in FIG. 4F, cell culture chamber 410 further comprises at least one of: a distal port 420 configured to allow for the removal of air bubbles from the cell culture chamber and/or as a recirculation port; a medial port 422 configured to function as a recirculation inlet port; and a proximal port 424 configured to function as a drain port for cell removal.

In further embodiments, provided herein is a cell culture chamber 410 for use in an automated cell engineering system, the cell culture chamber comprising a flat and non-flexible chamber, having a chamber height of about 0.5 cm to about 4 cm, and a cell-contacting surface 480. Suitably, at least 50% of the cell-contacting surface comprises a non-porous, gas-permeable material 482 comprising silicone.

In additional embodiments, the cell culture chamber further comprises at least one of: a distal port configured to allow for the removal of air bubbles from the cell culture chamber and/or as a recirculation port; a medial port configured to function as a recirculation inlet port; and a proximal port configured to function as a drain port for cell removal. Suitably, the cell culture chamber has a volume of about 50 ml to about 200 ml.

As described herein, in exemplary embodiments, the cell-contacting surface comprises a plurality of separate sections, each section comprising the non-porous, gas-permeable material. In suitable embodiments, the entire cell-contacting surface comprises the non-porous, gas-permeable material.

In further embodiments, the cell-contacting surface further comprises a surface coating on the cell-contacting surface selected from the group consisting of: a surface coating that activates a cell; a surface coating that modulates a biological pathway in a cell; a surface coating that enhances growth of a cell; and a surface coating that improves adhesion of a cell. Exemplary surface coatings are described herein.

In still further embodiments, provided herein is cassette 402 for use in an automated cell engineering system 400, comprising cell culture chamber 410 for carrying out activation, transduction and/or expansion of a cell culture, suitably an immune cell culture, having a chamber volume that is configured to house a cell culture and a satellite volume 430 for increasing the working volume of the cell culture chamber by providing additional volume for media and other working fluids without housing the cell culture (i.e., satellite volume does not contain any cells). Suitably, the satellite volume is fluidly connected to the cell culture chamber such that media is exchanged with the culture chamber without disturbing the cell culture. In exemplary embodiments, satellite volume is a bag, and in other embodiments, satellite volume is a non-yielding chamber. In embodiments, the satellite volume is between about 0.50 ml and about 300 ml, more suitably between about 150 ml and about 200 ml. FIG. 4D-4E show the position of a satellite volume 430 in cassette 602.

As described herein, the cell culture chamber 410 is suitably not a centrifugation chamber. That is, in embodiments, the cell culture chamber does not contain a portion or configuration that allows for the chamber to spin to generate a centripetal force, thereby separating the cells. Suitably, the cell culture chamber described herein remains largely stationary in the cassette.

Figure 5B:
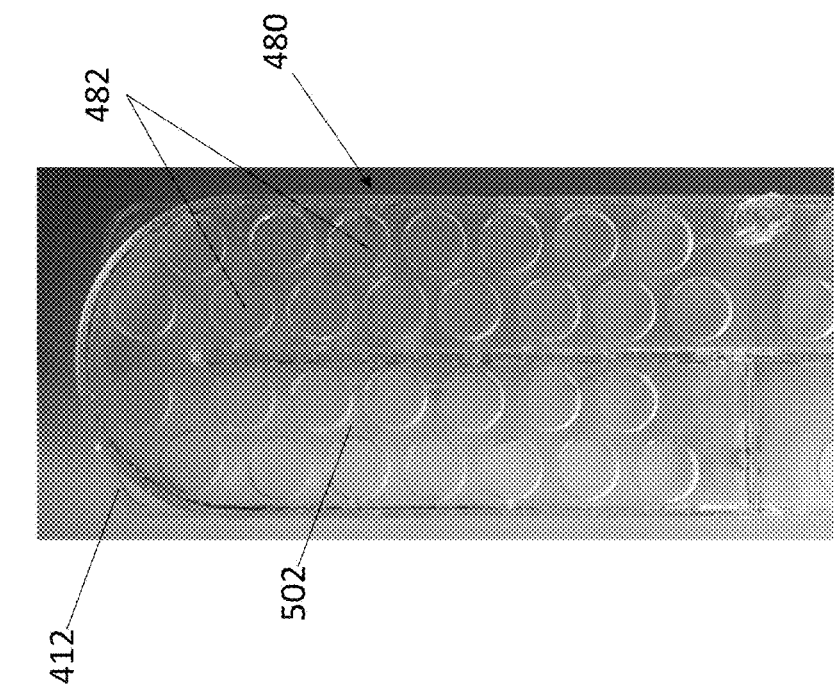
FIGS. 5A-5C show additional cell culture chambers in accordance with embodiments hereof.
Figure 5A:
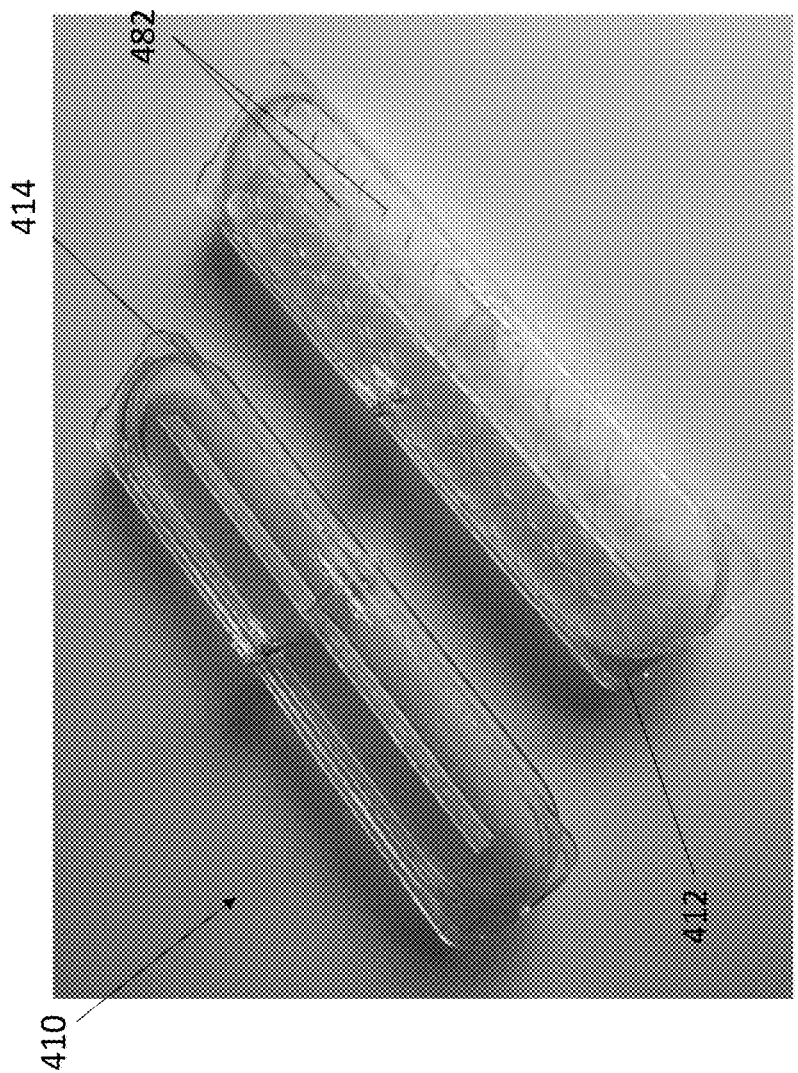
Figure 5C:
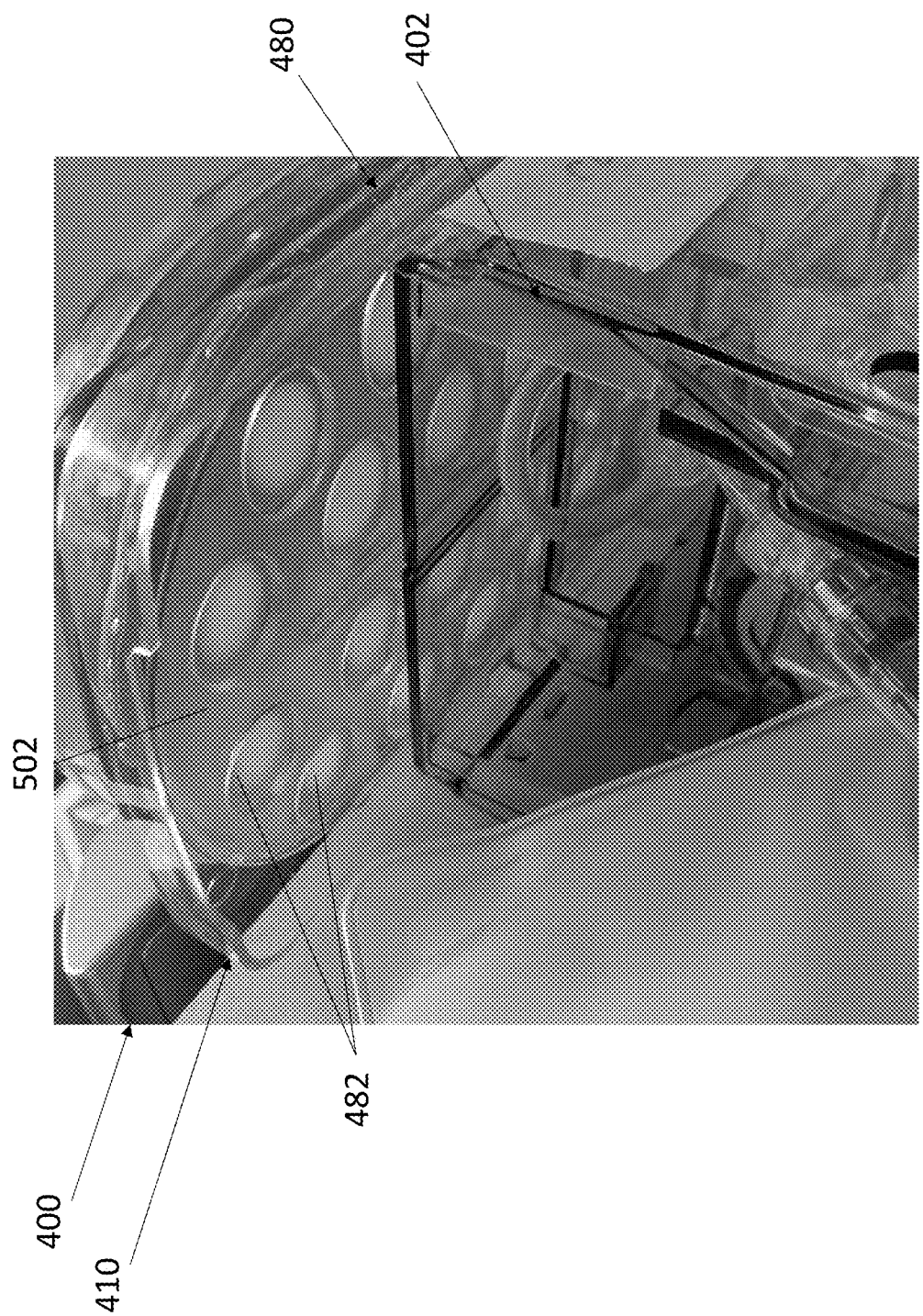

FIGS. 5A-5B show additional examples of cell culture chamber 410 that include structural sections 502 and sections or portions of non-porous, gas-permeable material 482 throughout the bottom 412 and/or top 414 of cell culture chamber 410. FIG. 5B shows bottom 412 of cell culture chamber 410, that makes up the cell-contacting surface 480 and includes sections or portions of non-porous, gas-permeable material 482 across the surface 480. These sections or portions can be of any shape, such as circles, squares, rectangles, triangles, other polygons or random shapes, or combinations of such shapes. The structural sections 502 provide support to the bottom 412, but still allows for a significant number of sections or portions of non-porous, gas-permeable material 482. FIG. 5C shows the incorporation of a cell culture chamber 410 that includes structural sections 502 and sections or portions of non-porous, gas-permeable material 482, integrated into a cassette 402 of an automated cell engineering system 400.

FIGS. 5D-5E show still further examples of a cell culture chamber 410 that include structural sections 520 and non-porous, gas-permeable material 482 throughout the bottom 412 and/or top 414 of cell culture chamber 410. Structural sections 520 of the embodiment shown in FIGS. 5D-5E can be a mesh, honeycomb, or similar structure that has open sections to allow increased use of a non-porous, gas-permeable material 482, but still maintain structural stability. In embodiments, structural sections 520 can be sandwiched between sheets of non-porous, gas-permeable material 482, providing the structural rigidity, but still allowing for the increase in gas permeability.

FIGS. 5F-5I shows various manufacturing techniques that can be used to create a cell culture chamber that includes a non-porous, gas-permeable material 482. For example, in FIG. 5F the thickness of non-porous, gas-permeable material 482 can be increased such that it by itself provides sufficient structural support for cell layer 530 and the required amount of media 540. In FIG. 5G, structural sections 520 of a support material (e.g., polystyrene of cell culture chamber 410) can be used to provide sufficient support. In FIG. 5H, this structural support can take the form of a mesh or honeycomb structure 550, which still limits flexing of non-porous, gas-permeable material 482. As described herein, in FIG. 5I, the support structure and the non-porous, gas-permeable material 482 can be cast together or infused together to create a non-porous, gas-permeable structural material 560. For example, a silicone-embedded plastic or custom EVO configuration can be utilized.

In still further embodiments, provided herein is a cassette 402 for use in an automated cell engineering system 400, comprising: optionally, a low temperature chamber 404, suitably for storage of a cell culture media; optionally, a high temperature chamber 406, suitably for carrying out activation, transduction and/or expansion of a cell culture, the high temperature chamber including a cell culture chamber 410; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber.

As described herein, suitably the cell culture chamber 410 is a flat and non-flexible chamber, having a low chamber height and a cell-contacting surface, and the cell culture chamber is maintained in a substantially planar orientation in the cassette. As described herein, "substantially planar" means that the cell culture chamber is maintained within about 15°, more suitably within about 10°, or about 5°, of horizontal (i.e., substantially parallel with respect to level ground). In embodiments, the cell culture chamber 410 can have a warped surface, e.g., on the order of about 1-5°, or about 3° of warp.

In still further embodiments, the cell culture chamber 410 can be oriented in a non-planar orientation (e.g., ±25-45°, or about ±30° from a horizontal planar orientation) which can result in a sedimented cell population with different cell densities at different areas of the chamber. The automated cell engineering system itself can also be tilted to align the cell culture chamber in a non-planar orientation.

Suitably, at least a portion of the cell-contacting surface comprises a non-porous, gas-permeable membrane, as described herein.

In embodiments, the cell culture chamber 410, and suitably cell-contacting surface 480 and non-porous, gas-permeable material 482 (if utilized), has a surface coating selected from the group consisting of: a surface coating that activates a cell; a surface coating that modulates a biological pathway in a cell; a surface coating that enhances growth of a cell; and a surface coating that improves adhesion of a cell, etc. Exemplary surface coatings are described herein. In embodiments, the cell culture chamber 410, and suitably cell-contacting surface 480 and non-porous, gas-permeable material 482 (if utilized) includes surface treatment as described herein.

In still further embodiments, provided herein is a cassette 402 for use in an automated cell engineering system 400, comprising: optionally, a low temperature chamber 404, e.g., for storage of a cell culture media; optionally, a high temperature chamber 406, e.g., for carrying out activation, transduction and/or expansion of a cell culture, the high temperature chamber including a cell culture chamber 410.

Suitably, the cassette further includes one or more fluidics pathways connected to the cell culture chamber, wherein the fluidics pathways provide recirculation, removal of waste and homogenous gas exchange and distribution of nutrients to the cell culture chamber without disturbing cells within the cell culture chamber. The cartridge 402 suitably further includes a fluidics pathway 460 connected to the cell culture chamber configured to introduce a surface coating material to the cell culture chamber. In such embodiments, the fluidics pathway to introduce a surface coating can be an internal component (e.g., a bag, reservoir or container) within the cassette that contains the coating material that is to be coated on the cell culture chamber. In other embodiments, the fluidics pathway can be a tubing or similar connection to an external valve for attachment to a syringe, bag, etc., for deliver of the surface coating material.

In suitable embodiments, the cell culture chamber for use in automated cell engineering systems as described herein includes a surface coating material already coated on one or more surfaces of the cell culture chamber.

However, in further embodiments, the surface coating materials can be provided via one or more fluidics pathways within (or external to) an automated cell engineering system, and then added to the cell culture chamber to generate the surface coating on the cell culture chamber. For example, an adhesion molecule or other coating material can be contained within a bag or chamber in the cassette/automated cell engineering system and then pumped into the cell culture chamber. Alternatively, the adhesion molecule can be added to cell culture chamber via one or more ports, using a syringe, bag, or similar device. The coating can then be dried on the cell culture chamber, and then excess removed prior to an optional wash with cell media or other to remove unbound surface coating material.

As described herein, in exemplary embodiments the cassette is pre-filled with one or more of a cell culture, a culture media, an activation reagent, and/or a vector, including any combination of these. In further embodiments, these various elements can be added later via suitable injection ports, etc.

As described herein, in embodiments, the cassettes suitably further include one or more of a pH sensor, a glucose sensor, an oxygen sensor, a lactate sensor, a cell counting module, a carbon dioxide sensor, a biomass sensor, an enzyme-based sensor, a fluorescent-base sensor, a microfluidic chip, a cell sorter, a lactic acid sensor/monitor, and/or an optical density sensor. The cassettes can also include one or more sampling ports and/or injection ports. Examples of such sampling ports and injection ports can include an access port for connecting the cartridge to an external device, such as analytical equipment, an electroporation unit or an additional media source.

Exemplary components of the cell engineering system include a gas control seal, a warming zone, actuators, a pivot for rocking or tilting the cell engineering system as desired, and low temperature zone for holding low temperature chamber. A user interface, which can include a bar code reader, and the ability to receive using inputs by touch pad or other similar device, can also be included.

Various sensors (e.g., pH sensor, dissolved oxygen sensor), as well as sampling/sample ports and various valves (control valves, bypass check valves), as well as one or more fluidic pathways, suitably comprising a silicone-based tubing component, connecting the components, can be positioned as required. As described herein, use of a silicone-based tubing component allows oxygenation through the tubing component to facilitate gas transfer and optimal oxygenation for the cell culture.

In some embodiments, the cell engineering system includes a plurality of chambers. In further embodiments, each of the activating, transducing, expanding, concentrating, and harvesting steps of the method for cells described herein is performed in a different chamber of the plurality of chambers of the cell engineering system. In some embodiments, the cells are substantially undisturbed during transfer from one chamber to another. In other embodiments, the steps of the method are performed in the same chamber of the cell engineering system, and the cell engineering system automatically adjusts the chamber environment as needed for each step of the method. Thus further allows for the cells to not be disturbed during the various steps.

In some embodiments, the cell engineering system has improved gas exchange compared with a flexible, gas-permeable bag for cell culture. In some embodiments, the cell engineering system includes gas exchange lines. The gas exchange lines may be made from a gas-permeable material such as, e.g., silicone. In some embodiments, the gas permeability coefficient of the gas exchange lines is higher than the permeability coefficient of the material used in the flexible, gas-permeable bag. In some embodiments, the cell engineering system recirculates oxygen throughout the substantially non-yielding chamber during the cell production methods. Thus, in some embodiments, the oxygen level of a cell culture in the cell engineering system is higher than the oxygen level of a cell culture in a flexible, gas-permeable bag. Higher oxygen levels may be important in the cell culture expansion step, as increased oxygen levels may support increased cell growth and proliferation.

In some embodiments, the cell engineering system continuously recirculates media throughout the chambers without disturbing the cells. For example, the cell engineering system can continuously replenish nutrients, remove waste, and circulate released cytokines and dissolved gases through the chamber, while the cells remain in the same area of the chamber. The continuous circulation can improve the uniform distribution of positive factors and uniform removal of negative factors, which reduces localized effects that are caused by uneven distribution, without disturbing the cells.

In some embodiments, the cell engineering system provides carbon dioxide throughout the chamber during the cell production methods (including CAR T production). $CO_2$ can help to maintain a target pH in the cell culture, which can be important for cell growth and proliferation. In some embodiments, the cell engineering system monitors the $CO_2$ level of the cell culture and adjusts the amount of $CO_2$ provided based on the measured $CO_2$ level. For example, as the cell culture increases, there is a corresponding increase in the amount of $CO_2$ produced by the cells, and the cell engineering system reduces the amount of $CO_2$ provided. The desired $CO_2$ level of the cell culture may be defined by the user, for example, about 1%, about 2%, about 3%, about 4%, about 5%, about 6%, about 7%, about 8%, about 9%, or about 10% $CO_2$. The $CO_2$ can also be turned off at certain points. Since the cell engineering system is constantly adjusting the amount of $CO_2$ provided based on the measured $CO_2$ level of the cell culture, the cell engineering system is able to maintain a desired $CO_2$ level throughout the production process. The amount of $CO_2$ in a cell culture may also affect the pH of the culture, since dissolved $CO_2$ generally acidifies a solution (through reacting with water to form carbonic acid). Thus, maintaining a steady $CO_2$ level in the cell culture may result in a more stable pH. Accordingly, in embodiments, the pH level of the cell culture remains substantially constant during the production process. In further embodiments, the pH level of the transduced cell culture remains substantially constant during the expansion step.

Yields from genetically modified immune cell production, including CAR T cell production, may be influenced by activation and transduction efficiency, as well as growth conditions of the cells. Activation efficiency can improve with more stable contact between the cells and the activation reagent. Movement of the cells throughout the culture vessel may lead to an uneven distribution of the cells, and thus create localized effects when activation reagent is added to the cell culture chamber. In contrast to a flexible culture bag, cells grown in a non-yielding chamber remain undisturbed during the activation process, which may contribute to a higher activation efficiency.

Growth conditions of the cell cultures may also improve cell yields. For example, higher oxygen levels in the cell engineering system, facilitated by highly gas-permeable tubing and continuous recirculation of oxygen in the cell culture chamber, may increase cell proliferation. The ability of the cell engineering system to constantly monitor the state of the cell culture, and make adjustments accordingly, may also be advantageous. For example, the cell engineering system can monitor the $CO_2$ $O_2$, $N_2$, and/or pH level of the cell culture and adjust the level of $CO_2$ $O_2$, or $N_2$. Nutrients can also be provided in a timely and consistent manner and distributed uniformly to the cell culture. Thus, the automated methods for producing various cell types, including connective tissue cells, cardiac cells, retinal cells, stem cells, as well as genetically modified immune cells, including CAR T cells, described herein advantageously results in higher cell yields compared with manual methods, or methods utilizing a flexible culture bag. Accordingly, in some embodiments, the method for automated production of the various cells described herein utilizing a cell engineering system as described herein, produces at least 10% more, at least 15% more at least 20% more, at least 25% more at least 30% more, at least 35% more at least 40% more, at least 45% more at least 50% more, at least 55% more at least 60% more, at least 65% more at least 70% more, at least 75% more at least 80% more, at least 85% more at least 90% more, at least 95% more or at least 100% more cells than a method utilizing a flexible, gas-permeable bag for cell culture. In embodiments, the number of cells produced by the methods described herein is at least about 2 billion (i.e., 2*10^9) cells, including at least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, or at least about 3.0 billion cells.

Figure 6B:
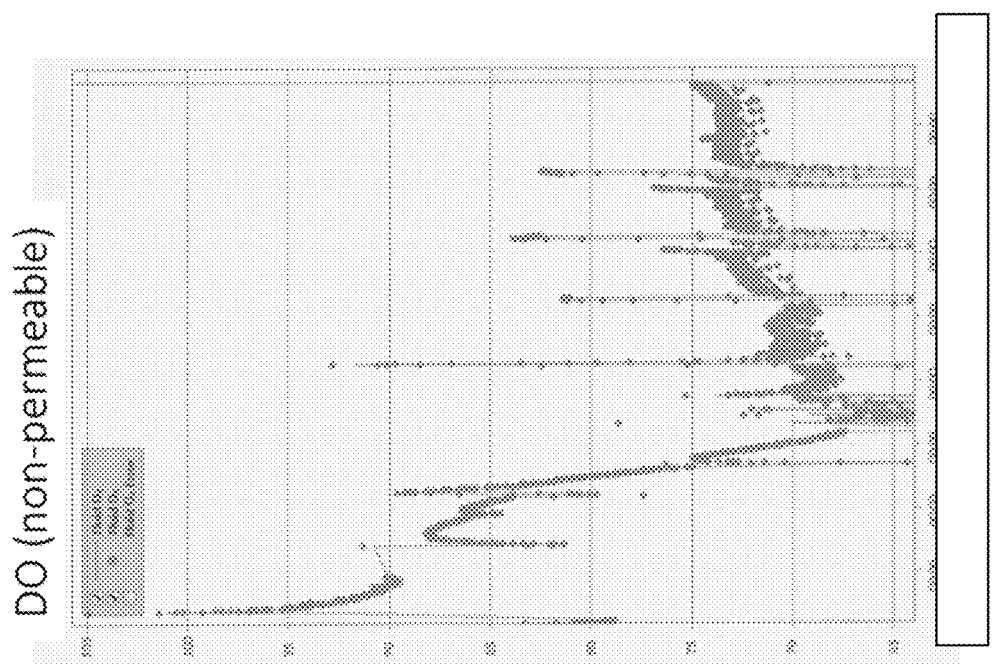
FIGS. 6A-6B show dissolved oxygen concentration measured with and without a non-porous, gas-permeable membrane.
Figure 6A:
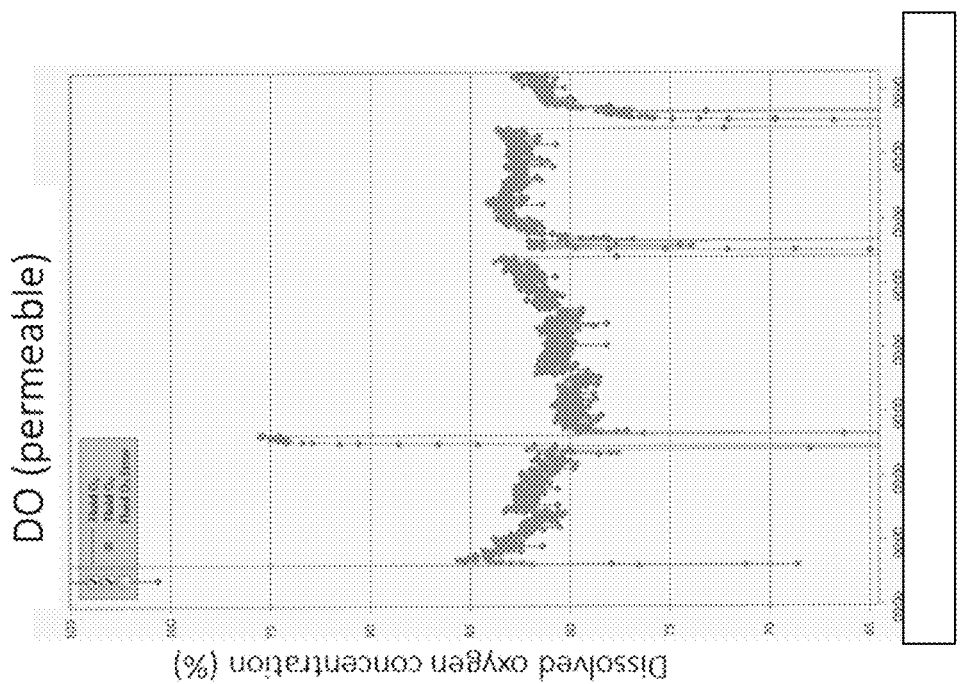

FIGS. 6A-6B show comparison of dissolved oxygen concentration measured in a cell culture chamber that includes a non-porous, gas-permeable membrane as described herein (FIG. 6A), in contrast with a chamber that does not include a gas-permeable membrane (FIG. 6B). As shown, dissolved oxygen concentration was greater with the incorporation of the gas-permeable membrane.

Figure 6D:
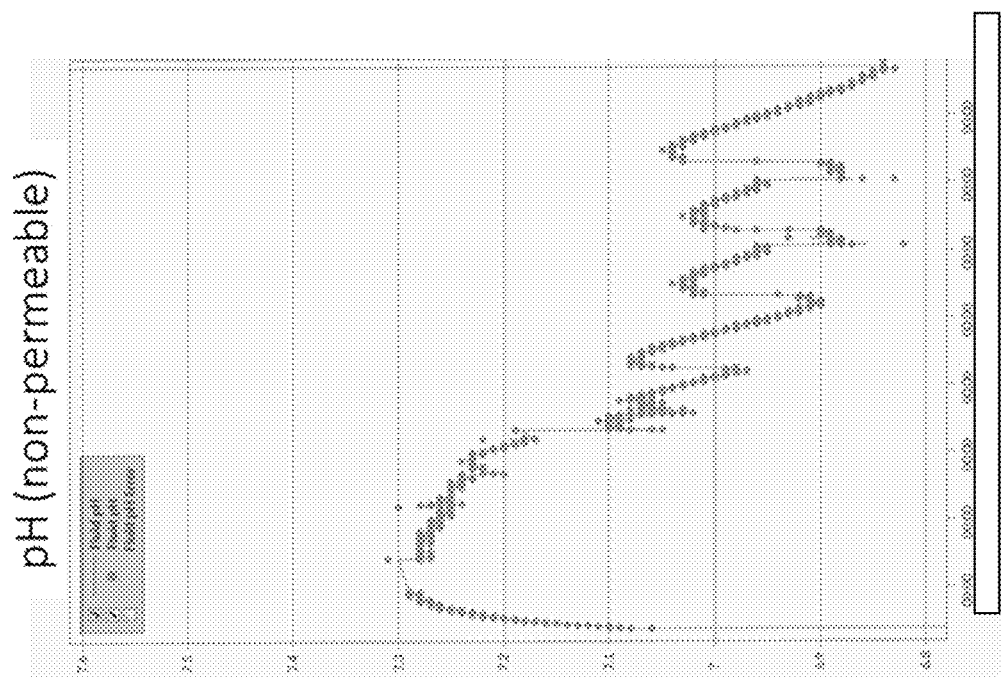
FIGS. 6C-6D show pH measured with and without a non-porous, gas-permeable membrane.
Figure 6C:
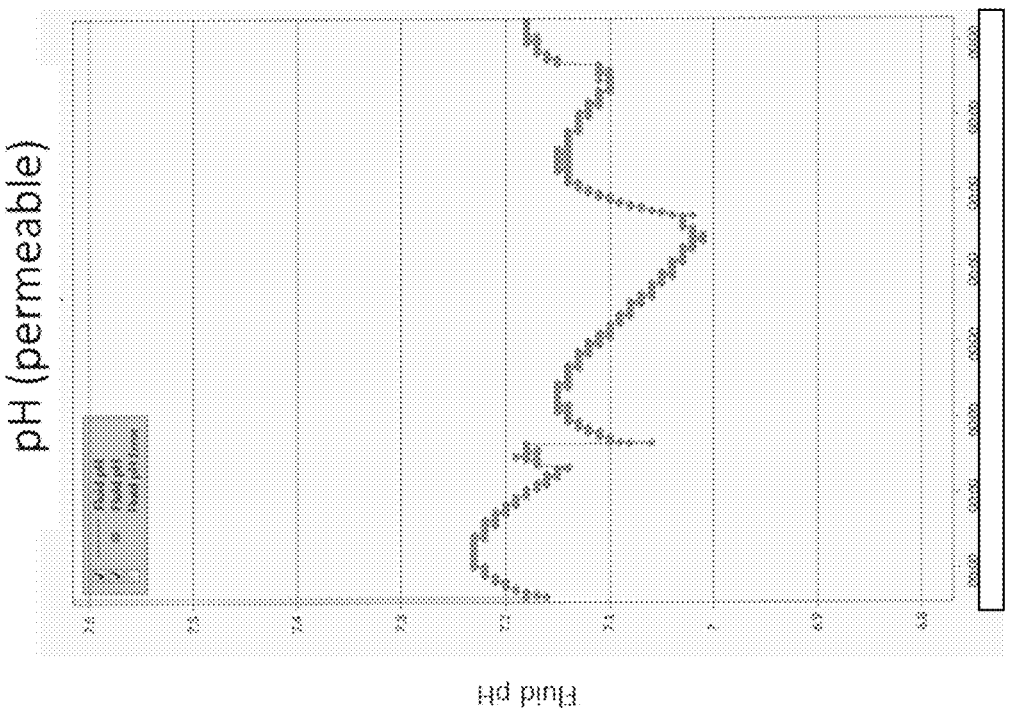

FIGS. 6C-6D show comparison of pH measured in a cell culture chamber that includes a non-porous, gas-permeable membrane as described herein (FIG. 6C), in contrast with a chamber that does not include a gas-permeable membrane (FIG. 6D). As shown, pH remains more consistent with the incorporation of the gas-permeable membrane.

Figure 7:
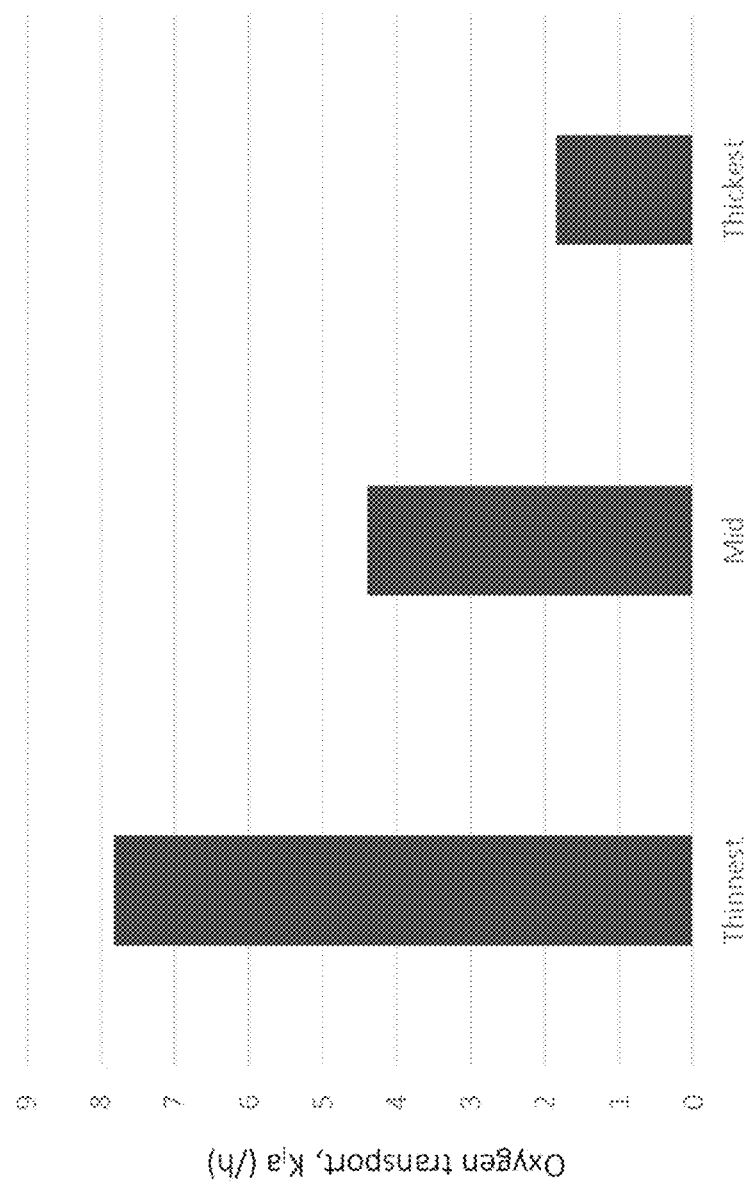
FIG. 7 shows the impact of the thickness of non-porous, gas-permeable material on oxygen transport.

FIG. 7 shows the impact on the thickness of non-porous, gas-permeable material 482, on oxygen transport. As shown, as the thickness of the gas-permeable material decreases (i.e., thinner material), the oxygen permeability increases.

Figure 8:
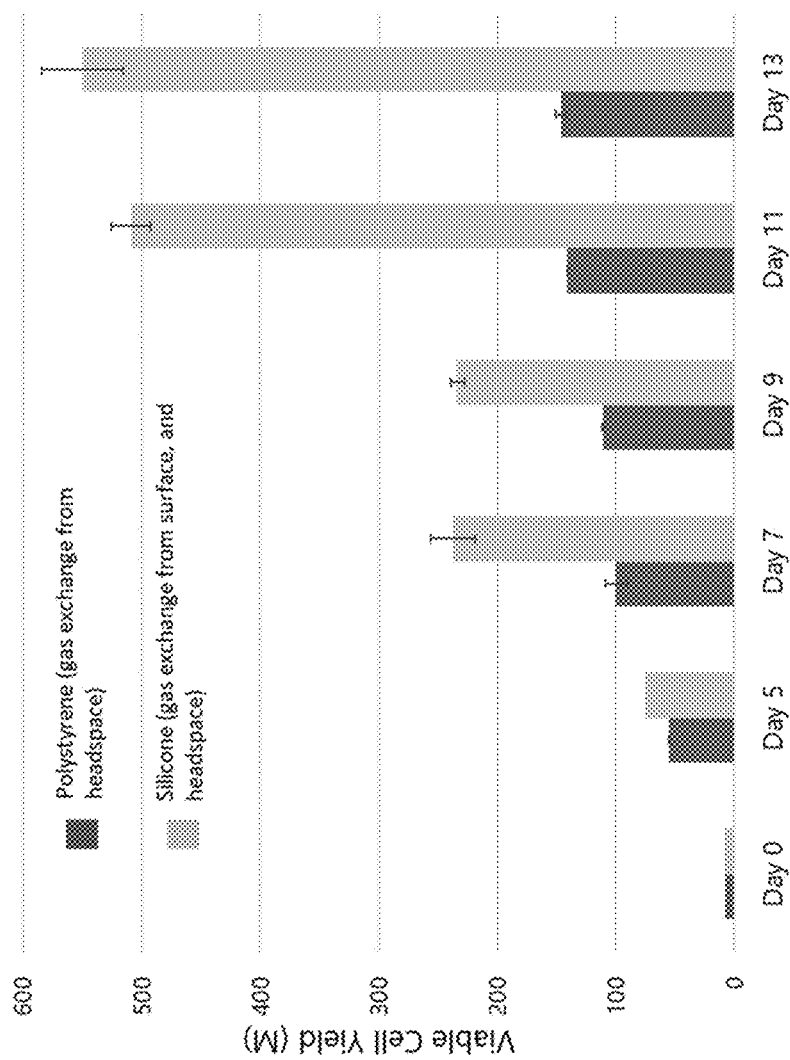
FIG. 8 shows the impact of increased gas exchange on cell growth.

FIG. 8 shows the impact of increased gas exchange on cell growth. For both polystyrene only cell culture chamber, and a cell culture chamber comprising a non-porous, gas-permeable material (silicone), the surface area, fluid height and feeding profile were kept the same. For the polystyrene only cell culture chamber, gas exchange was only provided via the headspace above the cell media in the cell culture chamber. The chamber that included the non-porous, gas-permeable material also allowed for gas exchange through the silicone. The final cell density of the polystyrene only cell culture chamber was 15 M cells/cm2, while the density with the increased gas permeability was 55 M cells/cm2, an increase of about 277%.

Additional Exemplary Embodiments

Embodiment 1 is a cell culture chamber for use in an automated cell engineering system, the cell culture chamber comprising: a flat and non-flexible chamber, having a low chamber height and a cell-contacting surface, wherein at least a portion of the cell-contacting surface comprises a non-porous, gas-permeable material.

Embodiment 2 includes the cell culture chamber of embodiment 1, wherein the cell culture chamber further comprises at least one of: a distal port configured to allow for the removal of air bubbles from the cell culture chamber and/or as a recirculation port; a medial port configured to function as a recirculation inlet port; and a proximal port configured to function as a drain port for cell removal.

Embodiment 3 includes the cell culture chamber of embodiment 1 or embodiment 2, wherein the cell-contacting surface comprises a plurality of separate sections, each section comprising the non-porous, gas-permeable material.

Embodiment 4 includes the cell culture chamber of embodiment 1 or embodiment 2, wherein at least about 50% of the cell-contacting surface comprises the non-porous, gas-permeable material.

Embodiment 5 includes the cell culture chamber of embodiment 1 or embodiment 2, wherein the entire cell-contacting surface comprises the non-porous, gas-permeable material.

Embodiment 6 includes the cell culture chamber of any one of embodiments 1-5, wherein the non-porous, gas-permeable material comprises silicone, fluoroethylene polypropylene (FEP), or ethyl vinyl olefin (EVO).

Embodiment 7 includes the cell culture chamber of any one of embodiments 1-6, having a chamber height of about 0.5 cm to about 4 cm.

Embodiment 8 includes the cell culture chamber of any one of embodiments 1-7, having a volume of about 50 ml to about 200 ml.

Embodiment 9 includes the cell culture chamber of any one of embodiments 1-8, wherein the cell culture chamber is not a centrifugation chamber.

Embodiment 10 includes the cell culture chamber of any one of embodiments 1-9, wherein the cell-contacting surface further comprises a surface coating on the cell-contacting surface selected from the group consisting of: a surface coating that activates a cell; a surface coating that modulates a biological pathway in a cell; a surface coating that enhances growth of a cell; a surface coating that improves adhesion of a cell; a surface coating that inhibits a cells; a surface coating that response to media conditions; and a surface coating that has controlled solubility.

Embodiment 11 includes the cell culture chamber of embodiment 10, wherein the surface coating comprises an adhesion molecule.

Embodiment 12 includes the cell culture chamber of embodiment 11, wherein the adhesion molecule is fibronectin or a modified fibronectin.

Embodiment 13 includes the cell culture chamber of any one of embodiments 1-12, wherein a portion of the cell-contacting surface further comprises a surface treatment.

Embodiment 14 is a cell culture chamber for use in an automated cell engineering system, the cell culture chamber comprising: a flat and non-flexible chamber, having a chamber height of about 0.5 cm to about 4 cm, and a cell-contacting surface, wherein at least 50% of the cell-contacting surface comprises a non-porous, gas-permeable material comprising silicone, fluoroethylene polypropylene (FEP), or ethyl vinyl olefin (EVO), and wherein the cell culture chamber further comprises at least one of: a distal port configured to allow for the removal of air bubbles from the cell culture chamber and/or as a recirculation port; a medial port configured to function as a recirculation inlet port; and a proximal port configured to function as a drain port for cell removal.

Embodiment 15 includes the cell culture chamber of embodiment 14, wherein the cell-contacting surface comprises a plurality of separate sections, each section comprising the non-porous, gas-permeable material.

Embodiment 16 includes the cell culture chamber of embodiment 14, wherein the entire cell-contacting surface comprises the non-porous, gas-permeable material.

Embodiment 17 includes the cell culture chamber of any one of embodiments 14-16, having a volume of about 50 ml to about 200 ml.

Embodiment 18 includes the cell culture chamber of any one of embodiments 14-17, wherein the cell culture chamber is not a centrifugation chamber.

Embodiment 19 includes the cell culture chamber of any one of embodiments 14-18, wherein the cell-contacting surface further comprises a surface coating on the cell-contacting surface selected from the group consisting of: a surface coating that activates a cell; a surface coating that modulates a biological pathway in a cell; a surface coating that enhances growth of a cell; a surface coating that improves adhesion of a cell; a surface coating that inhibits a cell; a surface coating that responds to media conditions; and a surface coating that has controlled solubility.

Embodiment 20 includes the cell culture chamber of embodiment 19, wherein the surface coating comprises an adhesion molecule.

Embodiment 21 includes the cell culture chamber of embodiment 20, wherein the adhesion molecule is fibronectin or a modified fibronectin.

Embodiment 22 includes the cell culture chamber of any one of embodiments 14-21, wherein a portion of the cell-contacting surface further comprises a surface treatment.

Embodiment 23 is a cassette for use in an automated cell engineering system, comprising: a high temperature chamber for carrying out activation, transduction and/or expansion of a cell culture, the high temperature chamber including a cell culture chamber; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber, wherein the cell culture chamber is a flat and non-flexible chamber, having a low chamber height and a cell-contacting surface, and the cell culture chamber is maintained in a substantially planar orientation in the cassette, and wherein at least a portion of the cell-contacting surface comprises a non-porous, gas-permeable material.

Embodiment 24 includes the cassette of embodiment 23, wherein the cell culture chamber further comprises at least one of: a distal port configured to allow for the removal of air bubbles from the cell culture chamber and/or as a recirculation port; a medial port configured to function as a recirculation inlet port; and a proximal port configured to function as a drain port for cell removal.

Embodiment 25 includes the cassette of embodiment 23 or 24, wherein the cell-contacting surface comprises a plurality of separate sections, each section comprising the non-porous, gas-permeable material.

Embodiment 26 includes the cassette of embodiment 23 or 24, wherein at least about 50% of the cell-contacting surface comprises the non-porous, gas-permeable material.

Embodiment 27 includes the cassette of embodiment 23 or claim 24, wherein the entire cell-contacting surface comprises the non-porous, gas-permeable material.

Embodiment 28 includes the cassette of any one of embodiments 23-27, wherein the non-porous, gas-permeable material comprises silicone, flouroethylenepolypropylene (FEP), or ethyl vinyl olefin (EVO).

Embodiment 29 includes the cassette of any one of embodiments 23-28, having a chamber height of about 0.5 cm to about 4 cm.

Embodiment 30 includes the cassette of any one of embodiments 23-29, having a volume of about 50 ml to about 200 ml.

Embodiment 31 includes the cassette of any one of embodiments 23-29, wherein the cassette does not include a centrifugation chamber.

Embodiment 32 includes the cassette of any one of embodiments 23-31, wherein the cell-contacting surface further comprises a surface coating on the cell-contacting surface selected from the group consisting of: a surface coating that activates a cell; a surface coating that modulates a biological pathway in a cell; a surface coating that enhances growth of a cell; a surface coating that improves adhesion of a cell; a surface coating that inhibits a cells; a surface coating that response to media conditions; and a surface coating that has controlled solubility.

Embodiment 33 includes the cassette of embodiment 32, wherein the surface coating comprises an adhesion molecule.

Embodiment 34 includes the cassette of embodiment 33, wherein the adhesion molecule is fibronectin or a modified fibronectin.

Embodiment 35 includes the cassette of any one of embodiments 23-34, wherein the cassette is pre-filled with culture media, activation reagent, and optionally a vector.

Embodiment 36 includes the cassette of any one of embodiments 23-35, further comprising one or more of a pH sensor, a glucose sensor, an oxygen sensor, a lactate sensor, a cell counting module, a carbon dioxide sensor, and/or an optical density sensor.

Embodiment 37 includes the cassette of any one of embodiments 23-36, further comprising one or more sampling ports and/or injection ports.

Embodiment 38 includes the cassette of any one of embodiments 23-37, further comprising an access port for connecting the cassette to an external device.

Embodiment 39 includes the cassette of embodiment 38, wherein the external device includes an electroporation unit or an additional media source.

Embodiment 40 includes the cassette of any one of embodiments 23-39, wherein one or more of the fluidic pathways comprise a silicone-based tubing component that allows oxygenation through the tubing component.

Embodiment 41 includes the cassette of any one of embodiments 23-40, wherein a portion of the cell-contacting surface further comprises a surface treatment.

Embodiment 42 includes the cassette of any one of embodiments 23-41, further comprising a low temperature chamber, for storage of a cell culture media.

Embodiment 43 is a cell culture chamber for use in an automated cell engineering system, comprising: a flat and non-flexible chamber, having a low chamber height; and a surface coating on the chamber selected from the group consisting of: a surface coating that activates a cell; a surface coating that modulates a biological pathway in a cell; a surface coating that enhances growth of a cell; a surface coating that improves adhesion of a cell; a surface coating that inhibits a cell; a surface coating that responds to media conditions; and a surface coating that has controlled solubility.

Embodiment 44 is the cell culture chamber of embodiment 43, wherein the cell is an immune cell.

Embodiment 45 is the cell culture chamber of embodiment 43, wherein the cell is a stem cell or a progenitor cell.

Embodiment 46 is the cell culture chamber of embodiment 45, wherein the stem cell is a pluripotent stem cell, a hematopoietic stem cell or a mesenchymal stem cell.

Embodiment 47 is the cell culture chamber of embodiment 43, wherein the cell is a connective tissue cell, a cardiac cell or a retinal cell.

Embodiment 48 is the cell culture chamber of any one of embodiments 43-47, wherein the cell culture chamber further comprises at least one of: a distal port configured to allow for the removal of air bubbles from the cell culture chamber and/or as a recirculation port; a medial port configured to function as a recirculation inlet port; and a proximal port configured to function as a drain port for cell removal.

Embodiment 49 is the cell culture chamber of any one of embodiments 43-48, wherein the surface coating comprises an adhesion molecule.

Embodiment 50 is the cell culture chamber of embodiment 49, wherein the adhesion molecule is fibronectin or a modified fibronectin.

Embodiment 51 is the cell culture chamber of any one of embodiments 43-50, having a height of about 0.5 cm to about 4 cm.

Embodiment 52 is the cell culture chamber of any one of embodiments 43-51, having a volume of about 50 ml to about 200 ml.

Embodiment 53 is the cell culture chamber of any one of embodiments 43-52, wherein the cell culture chamber is not a centrifugation chamber.

Embodiment 54 is the cell culture chamber of any one of embodiments 43-53, wherein a portion of the chamber further comprises a surface treatment.

Embodiment 55 is a cassette for use in an automated cell engineering system, comprising: a high temperature chamber for carrying out activation, transduction and/or expansion of a cell culture, the high temperature chamber including a cell culture chamber; and one or more fluidics pathways connected to the cell culture chamber, wherein the fluidics pathways provide recirculation, removal of waste and homogenous gas exchange and distribution of nutrients to the cell culture chamber without disturbing cells within the cell culture chamber, wherein the cell culture chamber is a flat and non-flexible chamber, having a low chamber height, and the cell culture chamber is maintained in a substantially planar orientation in the cassette, and wherein the cell culture chamber has a surface coating selected from the group consisting of: a surface coating that activates a cell; a surface coating that modulates a biological pathway in a cell; a surface coating that enhances growth of a cell; a surface coating that improves adhesion of a cell; a surface coating that inhibits a cell; a surface coating that responds to media conditions; and a surface coating that has controlled solubility.

Embodiment 56 is a cassette for use in an automated cell engineering system, comprising: a high temperature chamber for carrying out activation, transduction and/or expansion of a cell culture, the high temperature chamber including a cell culture chamber; wherein the cell culture chamber is a flat and non-flexible chamber, having a low chamber height, and the cell culture chamber is maintained in a substantially planar orientation in the cassette; one or more fluidics pathways connected to the cell culture chamber, wherein the fluidics pathways provide recirculation, removal of waste and homogenous gas exchange and distribution of nutrients to the cell culture chamber without disturbing cells within the cell culture chamber; and a fluidics pathway connected to the cell culture chamber configured to introduce a surface coating material to the cell culture chamber, the surface coating material selected from the group consisting of: a surface coating material that activates a cell; a surface coating material that modulates a biological pathway in a cell; a surface coating material that enhances growth of a cell; a surface coating material that improves adhesion of a cell; a surface coating material that inhibits a cell; a surface coating material that responds to media conditions; and a surface coating material that has controlled solubility.

Embodiment 57 is the cassette of claim 55 or claim 56, further comprising a low temperature chamber for storage of a cell culture media.

Embodiment 58 is the cassette of embodiment 55 or 56, wherein the cell is an immune cell.

Embodiment 59 is the cassette of embodiment 55 or 56, wherein the cell is a stem cell.

Embodiment 60 is the cassette of embodiment 59, wherein the stem cell is a pluripotent stem cell or a mesenchymal stem cell.

Embodiment 61 is the cassette of embodiment 55 or 56, wherein the cell is a connective tissue cell, a cardiac cell or a retinal cell.

Embodiment 62 is the cassette of any one of embodiments 55-61, wherein the cell culture chamber further comprises at least one of: a distal port configured to allow for the removal of air bubbles from the cell culture chamber and/or as a recirculation port; a medial port configured to function as a recirculation inlet port; and a proximal port configured to function as a drain port for cell removal.

Embodiment 63 is the cassette of any one of embodiments 55-62, wherein the surface coating material comprises an adhesion molecule.

Embodiment 64 is the cassette of embodiment 63, wherein the adhesion molecule is fibronectin or a modified fibronectin.

Embodiment 65 is the cassette of any one of embodiments 55-64, having a height of about 0.5 cm to about 4 cm.

Embodiment 66 is the cassette of any one of embodiments 55-65, having a volume of about 50 ml to about 200 ml.

Embodiment 67 is the cassette of any one of embodiments 55-66, wherein the cell culture chamber is not a centrifugation chamber, and the cassette does not comprise a centrifugation chamber.

Embodiment 68 is the cassette of any one of embodiments 55-67, wherein the cassette is pre-filled with culture media, activation reagent, the surface coating material, and optionally a vector.

Embodiment 69 is the cassette of any one of embodiments 55-68, further comprising one or more of a pH sensor, a glucose sensor, an oxygen sensor, a lactate sensor, a cell counting module, a carbon dioxide sensor, and/or an optical density sensor.

Embodiment 70 is the cassette of any one of embodiments 55-69, further comprising one or more sampling ports and/or injection ports.

Embodiment 71 is the cassette of any one of embodiments 55-70, further comprising an access port for connecting the cassette to an external device.

Embodiment 72 is the cassette of embodiment 71, wherein the external device includes an electroporation unit or an additional media source.

Embodiment 73 is the cassette of any one of embodiments 55-72, wherein one or more of the fluidic pathways comprise a silicon-based tubing component that allows oxygenation through the tubing component.

Embodiment 74 is the cassette of any one of embodiments 55-73, wherein a portion of the cell-contacting surface further comprises a surface treatment.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. A cassette for use in an automated cell engineering system as a removable and replaceable element, comprising:
   a. a high temperature chamber configured for carrying out activation, transduction and/or expansion of a cell culture at a temperature of between 35° C. to 40° C., the high temperature chamber including a cell culture chamber;
   b. a low temperature chamber configured for storage of a reagent at a temperature of between 4° C. to 8° C.;
   c. a thermal barrier adjacent the high temperature chamber and the low temperature chamber and separating the high temperature chamber from the low temperature chamber within the cassette; and
   d. one or more fluidics pathways connected to the cell culture chamber, wherein the fluidics pathways provide recirculation, removal of waste and homogenous gas exchange and distribution of nutrients to the cell culture chamber without disturbing cells within the cell culture chamber;
   wherein the cell culture chamber is a flat and non-flexible chamber, having a low chamber height and a cell-contacting surface, and the cell culture chamber is maintained in a substantially planar orientation in the cassette, and
   wherein at least a portion of the cell-contacting surface comprises a non-porous, gas-permeable material, and the cell-contacting surface further includes multiple structures cut or made into the cell-contacting surface to add surface area to increase cell adhesion, wherein the multiple structures are sandwiched between sheets of the non-porous, gas-permeable material.

2. The cassette of claim 1, wherein the cell culture chamber further comprises at least one of:
   i. a distal port configured to allow for the removal of air bubbles from the cell culture chamber and/or as a recirculation port;
   ii. a medial port configured to function as a recirculation inlet port; and
   iii. a proximal port configured to function as a drain port for cell removal.

3. The cassette of claim 1, wherein the cell-contacting surface comprises a plurality of separate sections, each section comprising the non-porous, gas-permeable material.

4. The cassette of claim 1, wherein at least about 50% of the cell-contacting surface comprises the non-porous, gas-permeable material.

5. The cassette of claim 1, wherein the entire cell-contacting surface comprises the non-porous, gas-permeable material.

6. The cassette of claim 1, wherein the non-porous, gas-permeable material comprises silicone, flouroethylene-polypropylene (FEP), or ethyl vinyl olefin (EVO).

7. The cassette of claim 1, having a chamber height of about 0.5 cm to about 4 cm.

8. The cassette of claim 1, having a volume of about 50 ml to about 200 ml.

9. The cassette of claim 1, wherein the cassette does not include a centrifugation chamber.

10. The cassette of claim 1, wherein the cell-contacting surface further comprises a surface coating on the cell-contacting surface selected from the group consisting of:
    i. a surface coating that activates a cell;
    ii. a surface coating that modulates a biological pathway in a cell;
    iii. a surface coating that enhances growth of a cell;
    iv. a surface coating that improves adhesion of a cell;
    V. a surface coating that inhibits a cell;
    vi. a surface coating that responds to media conditions; and
    vii. a surface coating that has controlled solubility.

11. The cassette of claim 10, wherein the surface coating comprises an adhesion molecule.

12. The cassette of claim 11, wherein the adhesion molecule is fibronectin or a modified fibronectin.

13. The cassette of claim 1, wherein the cassette is pre-filled with culture media, activation reagent, and optionally a vector.

14. The cassette of claim 1, further comprising one or more of a pH sensor, a glucose sensor, an oxygen sensor, a lactate sensor, a cell counting module, a carbon dioxide sensor, and/or an optical density sensor.

15. The cassette of claim 1, further comprising one or more sampling ports and/or injection ports.

16. The cassette of claim 1, further comprising an access port for connecting the cassette to an external device.

17. The cassette of claim 16, wherein the external device includes an electroporation unit or an additional media source.

18. The cassette of claim 1, wherein one or more of the fluidic pathways comprise a silicone-based tubing component that allows oxygenation through the tubing component.

19. The cassette of claim 1, wherein a portion of the cell-contacting surface further comprises a surface treatment.

20. The cassette of claim 1, wherein the low temperature chamber further includes a bag or other holder for the reagent.

* * * * *